United States Patent [19]

Buendia et al.

[11] 4,119,727
[45] Oct. 10, 1978

[54] NOVEL 11-DESOXY-PROSTAGLANDIN F$_2$ DERIVATIVES

[75] Inventors: Jean Buendia, Le Perreux-sur-Marne; Jeanine Nierat, Suresnes; Robert Deroy, Sceaux, all of France

[73] Assignee: Roussel Uclaf, Paris, France

[21] Appl. No.: 792,563

[22] Filed: May 2, 1977

[30] Foreign Application Priority Data

Apr. 30, 1976 [FR] France .............................. 76 12942
Jan. 18, 1977 [FR] France .............................. 77 01299

[51] Int. Cl.$^2$ ..................... A01N 9/00; C07D 333/24
[52] U.S. Cl. ............................. 424/275; 260/332.2 A
[58] Field of Search ................. 260/332.2 A; 424/275

[56] References Cited

U.S. PATENT DOCUMENTS

| | | | |
|---|---|---|---|
| 3,776,940 | 12/1973 | Just | 260/332.3 |
| 3,794,664 | 2/1974 | Just | 260/332.3 |
| 3,956,284 | 5/1976 | Hess | 260/332.3 |

*Primary Examiner*—A. Seigel
*Attorney, Agent, or Firm*—Hammond & Littell

[57] ABSTRACT

Novel 11-desoxy-prostaglandin F$_2$ derivatives of the formula

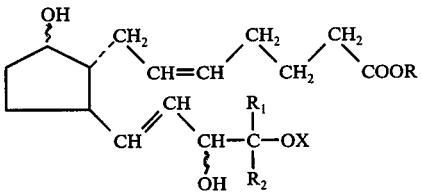

wherein R is selected from the group consisting of hydrogen, alkyl of 1 to 4 carbon atoms, an alkali metal, an equivalent of an alkaline earth metal, magnesium or organic amine base, R$_1$ and R$_2$ are individually seleced from the group consisting of hydrogen and methyl and X is selected from the group consisting of

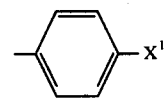

and a 5 to 6 membered heterocycle optionally substituted with at least one member of the group consisting of halogen, —CN and alkyl of 1 to 5 carbon atoms and X$^1$ is a 6 member heterocycle with the wavy lines indicating that the hydroxy may be in either one of the two possible α and β positions having hypotensive activity and process for their preparation.

18 Claims, No Drawings

NOVEL 11-DESOXY-PROSTAGLANDIN F₂ DERIVATIVES

STATE OF THE ART

French Pat. Nos. 2,289,179 and 2,145,601 disclose related prostaglandins.

OBJECTS OF THE INVENTION

It is an object of the invention to provide the novel prostaglandin derivatives of formula I.

It is another object of the invention to provide novel processes for the production of the compounds of formula I and to novel intermediates therefore.

It is a further object of the invention to provide novel hypotensive compositions and to provide a novel method of inducing hypotension and luteolysis in warm-blooded animals.

These and other objects and advantages of the invention will become obvious from the following detailed description.

THE INVENTION

The novel 11-desoxy-prostaglandin F₂ derivatives of the invention have the formula

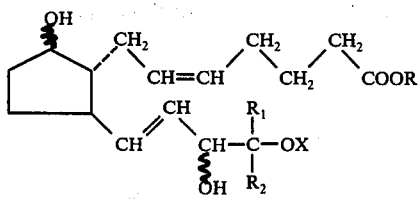

wherein R is selected from the group consisting of hydrogen, alkyl of 1 to 4 carbon atoms, an alkali metal, an equivalent of an alkaline earth metal, magnesium or organic amine base, $R_1$ and $R_2$ are individually selected from the group consisting of hydrogen and methyl and X is selected from the group consisting of

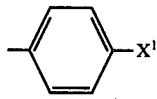

and a 5 to 6 membered heterocycle optionally substituted with at least one member of the group consisting of halogen, —CN and alkyl of 1 to 5 carbon atoms, and $X^1$ is a 6 member heterocycle with the wavy lines indicating that the hydroxy may be in either one of the two possible α and β positions.

Among the examples of R are methyl, ethyl, propyl, isopropyl, butyl, isobutyl, tert.-butyl, sodium, potassium, lithium, calcium, magnesium or organic bases such as trimethylamine, triethylamine, methylamine, propylamine, N,N-dimethylethanolamine and tris(hydroxymethyl)amino methane.

Examples of heterocycles of X are thienyl, furyl, thiazolyl, isothiazolyl, thiadiazolyl, oxadiazolyl, diazolyl, triazolyl, tetrazolyl, oxazolyl, pyridyl or pyrimidyl. The said heterocycles may be substituted with one or more substituents such as methyl, ethyl, propyl, isopropyl, butyl, isobutyl, tert.-butyl, pentyl, isopentyl, chloro, bromo, fluoro or cyano. $X^1$ may be tetrahydropyranyl, pyranyl or pyridyl.

Among the preferred compounds of formula I are products wherein R is hydrogen or tris(hydroxymethyl)amino methane, one of $R_1$ and $R_2$ is hydrogen and X is thienyl, furyl, thiadiazolyl or thiazolyl optionally substituted with at least one member of the group consisting of methyl and cyano and chlorine or X is 4-(4'-tetrahydropyranyl)-phenyl. The most preferred compounds of formula I are those wherein R is hydrogen or tris(hydroxymethyl)amino methane, one of $R_1$ and $R_2$ is hydrogen and X is thienyl, thiadiazolyl, thiazolyl or 4-(4'-tetrahydropyranyl)-phenyl.

Examples of preferred compounds of formula I are (8RS, 9SR, 12RS, 15RS) (5Z,13E) 9,15-dihydroxy-16-(3'-thienyloxy)-17,18,19,20-tetranor-prosta-5,13-dienoic acid and (8RS, 9SR, 12RS, 15RS) (5Z,13E) 9,15-dihydroxy-16-[3'-(5'-chloro)-thienyloxy]-17,18,19,20-tetranor-prosta-5,13-dienoic acid and their salts with tris(hydroxymethyl) amino methane.

The novel process of the invention for the preparation of a compound of formula I comprises reacting in the presence of a strong base a compound of the formula

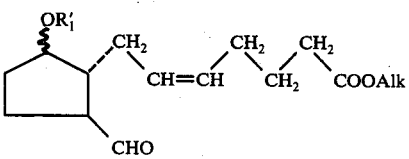

wherein Alk is alkyl of 1 to 4 carbon atoms and $R_1'$ is an acyl of an organic carboxylic acid with a phosphonate of the formula

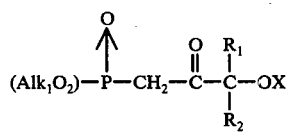

wherein $R_1$, $R_2$ and X have the above definitions and $Alk_1$ is alkyl of 1 to 4 carbon atoms to obtain a compound of the formula

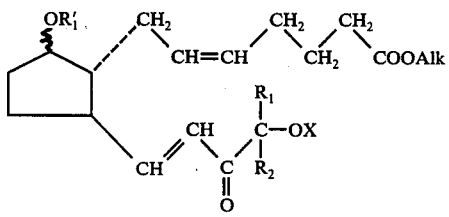

reacting the latter with a reducing agent to obtain a compound of the formula

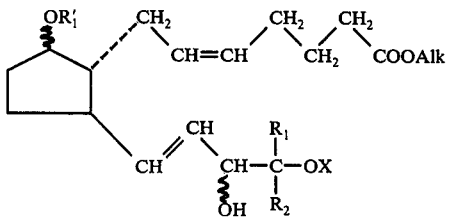

treating the latter with a base and then an acid to obtain a compound of the formula

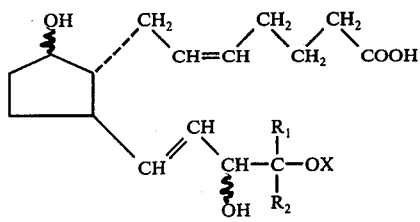

which is a compound of formula I wherein R is hydrogen and if desired the latter may be esterified to obtain a compound wherein R is alkyl of 1 to 4 carbon atoms or may be salified to obtain an alkali metal, alkaline earth metal, magnesium or organic amine salt thereof.

The phosphonates used to react with compounds of formula II are preferably those wherein $Alk_1$ is methyl but equally useful are those wherein $Alk_1$ is ethyl, propyl or butyl. The strong base used is preferably sodium hydride but strong bases such as sodium amide, sodium tert.-amylate or butyllithium may be used.

The reducing agent used to treat the compounds of formula III is preferably sodium borohydride or zinc but equally useful are other reducing agents such as sodium trimethoxy borohydride or lithium tris(sec-butyl)borohydride. The treatment of the compounds of formula IV is preferably effected with sodium hydroxide in ethanol followed by acidification with monosodium phosphate. However, other bases such as potassium hydroxide, barium hydroxide or lithium hydroxide may be used as well as other mineral or organic acids.

The esterification and salification of the compounds of formula I' may be effected by known methods. The esterification is effected, for example, with the acid and the desired alkanol in the presence of an acid agent. The salification may be effected by reacting the acid with a mineral base such as sodium hydroxide or potassium hydroxide or an organic base such as triethylamine, preferably in a solvent or mixture of solvents such as water, ethyl ether, acetone or ethanol.

Another facet of the invention is a process for the preparation of a compound of formula II comprising reacting in the presence of a base a compound of the formula

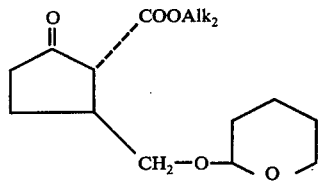

with a compound of the formula

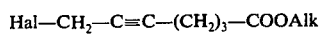

wherein Hal is a halogen and $Alk_2$ is alkyl of 1 to 4 carbon atoms to obtain a compound of the formula

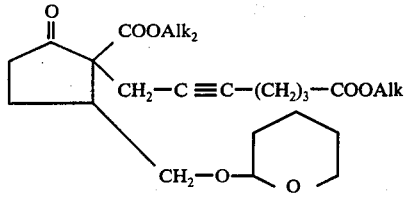

treating the latter with a reactant to remove an alkoxycarbonyl group to obtain a compound of the formula

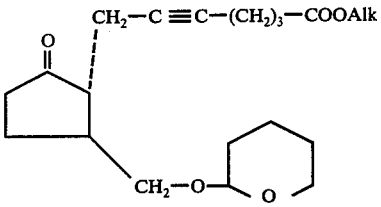

treating the latter with hydrogen in the presence of a catalyst to obtain a compound of the formula

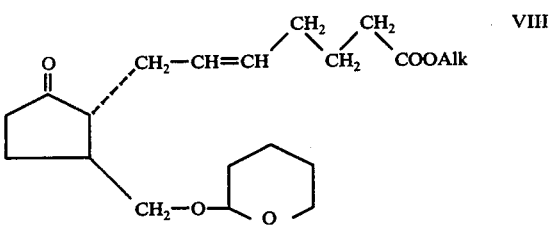

treating the latter with a reducing agent to obtain a compound of the formula

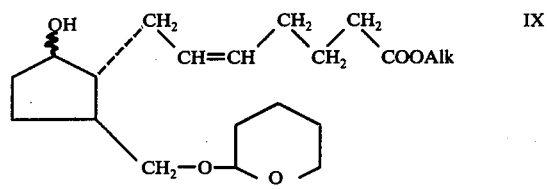

which if desired may be separated into its α or β-isomers and reacting the product of formula IX with an acid anhydride of the formula $(R_1')_2O$ or an acid chloride of the formula $R_1'Cl$ to obtain a compound of the formula

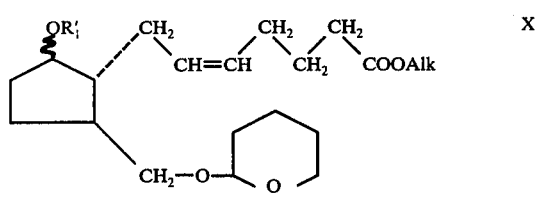

treating the latter with an acid to obtain a compound of the formula

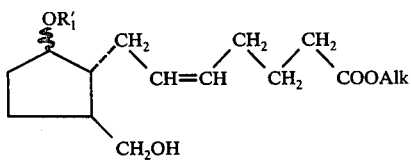

and reacting the latter with an oxidation agent to obtain the corresponding compound of formula II.

In a preferred mode of the process, the compound reacted with the compound of formula V is the bromide, but the chloride or iodide can also be used and the base is preferably potassium carbonate but other bases such as potassium hydride or potassium tert.-butylate may also be used. The alkoxy carbonyl group is preferably removed with sodium cyanide but equally useful is lithium chloride. The hydrogenation catalyst is preferably palladium or barium sulfate in the presence of quinoline but equally useful is platinum or palladized activated carbon.

The reducing agent used to treat the compounds of formula VIII is preferably lithium tris(sec-butyl)borohydride but also useful are other reducing agents such as sodium borohydride or sodium trismethoxy borohydride. The products of formula IX are preferably reacted with acetic acid anhydride to form the corresponding acetate but other acyl groups may be used and the acid chlorides such as benzoyl chloride may be used. Preferably, $R_1'$ is formyl, acetyl, trichloroacetyl or benzoyl. The acid used to treat the compounds of formula X is preferably hydrochloric acid but other acids such as acetic acid, oxalic acid or sulfuric acid may be used. The oxidation agent is preferably chrome oxide in pyridine but other oxidizing agents such as chrome oxide in triethylamine or in collidine may also be used.

The compounds of formulae IX, X, XI, II and III contain a free or protected hydroxy group which can be in one of the $\alpha$ or $\beta$ positions to the carbon atoms to which they are attached and the products if in the form of mixtures of the isomers can be separated by known physical methods such as chromatography. Preferably, the isomers of formula IX are separated by chromatograhy. One obtains from the following process starting from a compound of formula IX containing only a single isomer a compound of formula II also containing a single isomer.

The products of formulae IV and I' contain two hydroxy groups and preferably the transformation of compounds of formula III into compounds of formula IV gives rise to a mixture of the 2 isomers. Preferably, a second separation by chromatography is effected on the compounds of formula IV to separate the products of formula IV which will lead to products of formula I' with a single isomer.

The products of formula I exist in the form of racemic mixtures or optically active isomers with the latter being separated by the usual methods such as resolution of acids as salts with optically active bases.

The novel hypotensive compositions of the invention are comprised of an hypotensively effective amount of at least one compound of formula I and an inert pharmaceutical carrier. The compositions may be in the form of tablets, dragees, gelules, granules, suppositories and injectable solutions or suspensions. Examples of suitable carriers are talc, arabic gum, lactose, starch, magnesium stearate, cacao butter, aqueous or non-aqueous vehicles, fatty bodies of animal or vegetable origin, paraffinic derivatives, glycols, preservatives, diverse wetting agents, dispersants and emulsifiers.

The compositions have hypotensive activity and contracturant activity on smooth muscles and the hypotensive activity is more prolonged than the activity of natural prostaglandins. The compositions are therefore useful for the treatment of hypertension and circulatory troubles or as ocytocic. The compositions also have a interesting luteolytic activity and are therefore useful for the synchronization of estrus in different animal species such as cows, sheep and mares.

The preferred hypotensive compositions contain (8RS, 9RS, 12RS, 15RS)(5Z,13E) 9,15-dihydroxy-16-(3'-thienyloxy)-17,18,19,20-tetranor-prosta-5,13-dienoic acid and (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid and their tris (hydroxymethyl)-aminomethane salts. The preferred compositions for the synchronization of estrus in mammals contain the same compositions.

The novel method of the invention for inducing hypotensive activity in warm-blooded animals, including humans, comprises administering to warm-blooded animals an hypotensively effective amount of at least one compound of formula I. The compounds may be administered orally, rectally or parentarelly or topically by aerosol. The usual useful dose is 0,001 to 0,060 mg/kg depending upon the compound or method of administration. For example, administration of 50 μg to 10 mg of the two preferred compounds in the form of their tris(hydroxymethyl)amino methane salts by slow perfusion to humans is adequate.

The novel method of effecting luteolysis in farm animals comprises administering a luteolysis effective amount of at least one compound of formula I. The compounds are preferably administered intramuscularly and with bovines a useful dose is 5 mg.

The novel intermediates of the invention have the formulae

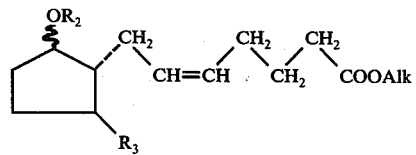

and

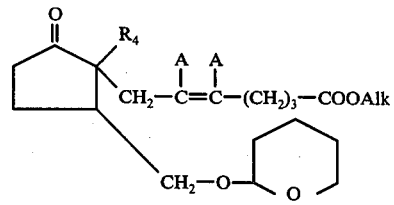

wherein $R_2$ is hydrogen or $R_1'$, $R_1'$ is an acyl or an organic carboxylic acid of 1 to 10 carbon atoms, $R_3$ is $\alpha$-tetrahydropyranyloxy methyl, hydroxy methyl or formyl with the proviso that when $R_2$ is hydrogen, $R_3$ is $\alpha$-tetrahydropyranyloxymethyl, Alk is alkyl of 1 to 4 carbon atoms, $R_4$ is hydrogen or —COOAlk$_2$, Alk$_2$ is alkyl of 1 to 4 carbon atoms and the As are hydrogen or together form a triple bond with the proviso that $R_4$ is hydrogen when the As are hydrogen.

The compounds of formula V may be prepared by reacting

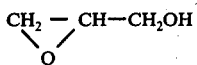

with dihydropyran in the presence of an acid such as p-toluene sulfonic acid to obtain a compound of the formula

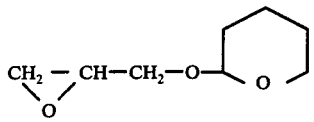

reacting the latter with an alkyl acetylacetate with the alkyl having 1 to 4 carbon atoms in the presence of a strong base such as a mixture of sodium hydride-butyllithium to obtain a compound of the formula

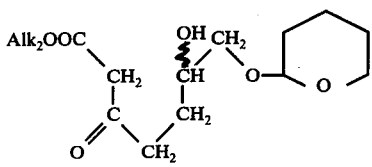

reacting the latter with an oxidation agent such as a complex of chrome oxide-pyridine to obtain a compound of the formula

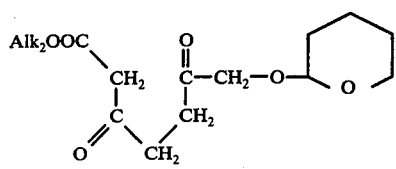

treating the latter with a base such as sodium bicarbonate to obtain a compound of the formula

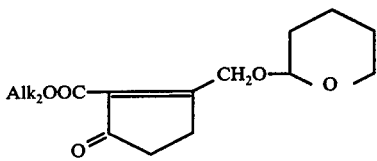

and treating the latter with hydrogen in the presence of a catalyst to obtain the corresponding compound of formula V.

The compounds of the formula

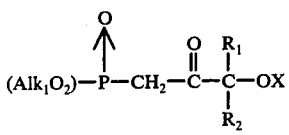

may be prepared by reacting a compound of the formula

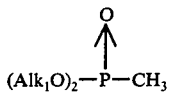

with a compound of the formula

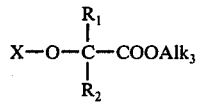

wherein $Alk_3$ is alkyl of 1 to 4 carbon atoms in the presence of a strong base. The latter products which are not known may be prepared by reacting a compound of the formula

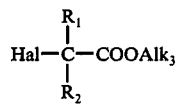

when Hal is a halogen with a compound of X-OH or a compound of the formula XBr with a compound of the formula

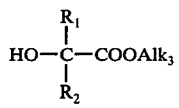

In the following examples there are described several preferred embodiments to illustrate the invention. However, it should be understood that the invention is not intended to be limited to the specific embodiments.

EXAMPLE 1

(8RS, 9SR, 12RS, 15SR)(5Z,13E) 9,15-dihydroxy-16-(3'-thienyloxy)-17,18,19,20-tetranor-prosta-5,13-dienoic acid STEP A: 1,2-epoxy-3α-tetrahydropyranyloxy-propane A solution of 3.9 g of glycidol (2,3-epoxy-1-propanol), 18.5 ml of dihydropyran and 150 mg of p-toluene sulfonic acid was heated at 40° C. for 30 minutes after which another 150 mg of p-toluene sulfonic acid was added. After 15 minutes, the mixture was neutralized at room temperature with potassium carbonate and the mixture was filtered. The filtrate was washed with ethyl acetate and was evaporated to dyrness under reduced pressure to obtain 8.48 g of 1,2-epoxy-3α-tetrahydropyranyloxy-propane with Rf = 0.6 (8-2 cyclohexane-ethyl acetate).

STEP B: methyl 3-keto-6-hydroxy-7α-tetrahydropyranyloxyheptanoate 3.554 g of sodium hydride in a 50% oily suspension in 16 ml of anhydrous tetrahydrofuran were added over 30 minutes at 0° C. to a solution of 8 ml of methyl acetylacetate and 16 ml of anhydrous tetrahydrofuran and then 39 ml butyllithium were added at 0° C. over 30 minutes. The mixture was stirred for 30 minutes and was then cooled to −70° C. The solution was added over 45 minutes to a solution at 0° C. of 5.8 g of the product of Step A in 16 ml of tetrahydrofuran and the mixture was stirred for 3½ hours. The mixture was poured into an excess of a concentrated, iced solution of monosodium phosphate and the mixture was stirred for 10 minutes. The mixture was extracted with ethyl acetate and the extracts were washed until the wash waters were neutral. After evaporation of the solvent, 16.9 g of an oil were recovered and was purified by chromatography over silica gel and was eluted with a 6-4 cyclohexane-ethyl acetate mixture to obtain 8.02 g of pure methyl 3-keto-6-hydroxy-7α-tetrahydropyranyloxy-heptanoate with an Rf = 0.15.

STEP C: methyl 3,6-dioxo-7α-tetrahydropyranyloxy-heptanoate 6 g of chromic acid were slowly added to a solution of 9.7 ml of pyridine in 148 ml of methylene chloride and after stirring for 15 minutes, a solution of 1.1 g of the product of Step B in 10 ml of methylene chloride were added. After 15 minutes, 150 ml of ether were added thereto and the mixture was filtered. The filtrate was washed with ether and was evaporated to dryness to obtain 1.3 g of raw product. The latter was purified by chromatography over silica gel and was eluted with an 8-2 methylene chloride-ethyl acetate mixture to obtain 473 mg of pure methyl 3,6-dioxo-7α-tetrahydropyranyloxy-heptanoate with an Rf = 0.45.

STEP D: methyl 2-(α-tetrahydropyranyloxymethyl)-5-oxo-1-cyclopentene carboxylate A solution of 291 mg of sodium bicarbonate in 72 ml of distilled water and a solution of 220 mg of the raw product of Step C in 2.4 ml of methylene chloride were vigorously stirred together for 30 minutes and the mixture was adjusted to a pH of 3 with oxalic acid. The mixture was saturated with sodium chloride and was extracted with methylene chloride. The extracts were evaporated to dryness to obtain 205mg of methyl 2-(α-tetrahydropyranyloxymethyl)-5-oxo-1-cyclopentene carboxylate.

STEP E: methyl (1RS, 5SR) 2-oxo-5-(α-tetrahydropyranyloxymethyl)-cyclopentane carboxylate A mixture of 215 mg of the product of Step D, 10 ml of methanol and 21 mg of 10% palladized carbon was stirred under a hydrogen atmosphere for 40 minutes during the theoretical amount of hydrogen was absorbed and the mixture was filtered. The filtrate was washed with ethyl ether and was evaporated to dryness to obtain 172 mg of an oil which was chromatographed over silica gel. Elution with a 1-1 cyclohexane-ethyl acetate mixture yielded 122 mg of methyl (1RS, 5SR) 2-oxo-5-(α-tetrahydropyranyloxymethyl)-cyclopentane carboxylate.

STEP F: ethyl (1'RS and SR, 5'SR) 7-[1'-carboxymethyl-2'-oxo-5'-(α-tetrahydropyranyloxymethyl)-cyclopentane]-5-heptynoate A mixture of 201 g of the product of Step E, 10 ml of anhydrous acetone and 130 mg of anhydrous potassium carbonate was stirred under nitrogen at room temperature for one hour and then a mixture of 219.5 mg of ethyl 7-bromo-5-heptynoate in 1 ml of anhydrous acetone was added thereto. The mixture was refluxed for 3½ hours and the acetone was then evaporated under reduced pressure. The residue was taken up in a saturated monosodium phosphate solution and the mixture was extracted with ethyl acetate. The organic extracts were washed and dried to obtain 393 mg of raw product which was chromatographed over silica gel. Elution with a 60-40 cyclohexane-ethyl acetate mixture containing 0.1% of triethylamine yielded 274.5 mg of pure ethyl (1'RS and SR, 5'SR) 7-[1'-carboxymethyl-2'-oxo-5'-(α-tetrahydropyranyloxymethyl)-cyclopentane]-5-heptynoate.

STEP G: ethyl (1'RS, 5'SR) 7-[2'-oxo-5'-(α-tetrahydropyranyloxymethyl)-cyclopentane]-5-heptynoate A mixture of 246 mg of the product of Step F and 10 ml of anhydrous hexamethylphosphorotriamide and 64 mg of sodium cyanide was heated at 75° C. under a slight current of nitrogen for 3 hours and was then cooled and chromatographed over silica gel. Elution with a 60-40 cyclohexane-ethyl acetate mixture containing 0.1% of triethylamine yielded 183.2 mg of ethyl (1'RS, 5'SR)-7-[2'-oxo-5'-(α-tetrahydropyranyloxymethyl)-cyclopentane]-5-heptynoate.

STEP H: ethyl (1'RS, 5'SR) (5Z) 7-[2'-oxo-5'-(α-tetrahydropyranyloxymethyl)-cyclopentane]-5-heptenoate A mixture of 183.2 mg of the product of Step G, 15 ml of ethyl acetate, 3 ml of methanol and 65 mg of 5% palladized barium sulfate doped with 4 drops of quinoline was rapidly hydrogenated at normal pressure in 15 minutes and the mixture was filtered. The catalyst was washed with ethyl acetate and the quinoline was separated by chromatography over silica gel and elution with a 70-30 cyclohexane-ethyl acetate mixture containing 0.1% of triethylamine to obtain 159.7 mg of ethyl (1'RS, 5'SR) (5Z) 7-[2'-oxo-5'-(α-tetrahydropyranyloxymethyl)-cyclopentane]-5-heptenoate.

STEP I: ethyl (1'RS, 2'SR, 5'SR) (5Z) 7-[2'-hydroxy-5'-(α-tetrahydropyranyloxymethyl)-cyclopentane]-5-heptenoate 0.4 ml of a molar solution of tris (sec) butyllithium borohydride in tetrahydrofuran was slowly added under nitrogen to a solution of 125.9 mg of the product of Step H in 10 ml of anhydrous tetrahydrofuran kept at −78° C. and the mixture was stirred at −78° C. for 45 minutes. 0.5 ml of a saturated solution of monosodium phosphate was added to effect hydrolysis and the mixture was added to a saturated aqueous sodium chloride solution. The aqueous phase was extracted with ethyl acetate and the organic phase was washed, dried and evaporated to dryness to obtain 206.5 mg of raw product. The latter was chromatographed over silica gel and was eluted with a 60-40 cyclohexane-ethyl acetate mixture containing 0.1% triethylamine to obtain 111.5 mg of ethyl (1'RS, 2'SR, 5'SR) (5Z) 7-[2'-hydroxy-5'-(α-tetrahydropyranyloxymethyl)-cyclopentane]-5-heptenoate.

STEP J: ethyl (1'RS, 2'SR, 5'SR) (5Z) 7-[2-acetoxy-5'-(α-tetrahydropyranyloxymethyl)-cyclopentane]-5-heptenoate A mixture of 100.9 mg (0.285 mm) of the product of Step I, 3 ml of methylene chloride, 0.1 ml of acetic acid anhydride, 0.2 ml of triethylamine and a few crystals of dimethylamino pyridine was stirred under nitrogen at room temperature for 1 hour and a saturated monosodium phosphate solution was added thereto with stirring. The mixture was extracted with ether and the ether extracts were washed with water, dried and evaporated to dryness to obtain 127.6 mg of raw oil. The latter was chromatographed over silica gel and was eluted with a 60-40 cyclohexane-ethyl acetate mixture containing 0.1% of triethylamine to obtain 107.2 mg of ethyl (1'RS, 2'SR, 5'SR) (5Z) 7-(2'acetoxy-5'-(α-tetrahydropyranyloxymethyl)-cyclopentane]-5-heptenoate.

STEP K: ethyl (1'RS, 2'SR, 5'SR) (5Z) 7-(2'-acetoxy-5'-hydroxymethyl-cyclopentane)-5-heptenoate A mixture of 131 mg of the product of Step J, 2 ml of ethanol, 0.2 ml of dioxane, 0.2 ml of water and a few drops of N hydrochloric acid to obtain a pH of 2 was heated at 55° C. under nitrogen for 5 hours and a few drops of disodium phosphate were added to adjust the pH to 4. The mixture was evaporated to dryness and the residue was taken up in aqueous sodium chloride solution. The mixture was extracted with ethyl acetate and the extracts were washed, dried and evaporated to dryness. The residue was purified over silica gel and was eluted with a 60–40 cyclohexane-ethyl acetate mixture to obtain 86 mg of ethyl (1'RS, 2'SR, 5'SR) (5Z) 7-(2'-acetoxy-5'-hydroxymethyl-cyclopentane)-5-heptenoate.

STEP L: ethyl (1'RS, 2'SR, 5'SR) (5Z) 7-(2'-acetoxy-5'-formyl-1'-cyclopentyl)-5-heptenoate 945 mg of chromium oxide were added in small portions under nitrogen at room temperature to a solution of 1.496 g of anhydrous pyridine in 20 ml of methylene chloride and the mixture was stirred for 30 minutes. A solution of 459.3 mg of the product of Step K in 1 ml of methylene chloride was added all at once to the reaction mixture and the mixture was rinsed with 1 supplementary ml. The mixture was strongly stirred for 45 minutes at room temperature and celite was added while contuining the agitation. The mixture was diluted with ether and was filtered. The product was dried over magnesium sulfate and was washed with ether to obtain 439.9 mg of raw ethyl (1'RS, 2'SR, 5'SR) (5Z) 7-(2-acetoxy-5-formyl-1'-cyclopentyl)-5-heptenoate which was used as is for the next steps.

STEP M: Ethyl(8RS, 9SR, 12RS, 15SR) (5Z, 13E) 9-acetoxy-15-hydroxy-16-(3'-thienyloxy)-17,18,19,20-tetranor-prosta-5,13-dienoate and ethyl (8RS, 9SR, 12RS, 15RS) (5Z, 13E) 9-acetoxy-15-hydroxy-16-(3'-thienyloxy)-17,18,19,20-tetranor-prosta-5,13-dienoate 220 ml of a 20% solution of butyllithium in hexane were added dropwise at −70° C. under an inert atmosphere to a mixture of 89 g of dimethyl methyl phosphonate in 250 ml of tetrahydrofuran and after 2½ hours, a mixture of 40.6 g of methyl 3-thienyloxy acetate in 100 ml of tetrahydrofuran cooled to −70° C. was added dropwise to the reaction mixture. The mixture was stirred for 2 hours and was then neutralized with 52 ml of glacial acetic acid. The mixture was evaporated to dryness under reduced pressure and the residue was taken up in chloroform. The solution was washed, dried and evaporated to dryness to obtain 70.2 g of an oil. The latter was chromatographed over silica gel and was eluted with a 1-1 toluene-ethyl acetate mixture to obtain 42 g of dimethyl 2-oxo-3-(3-thienyloxy)-propylphosphonate.

A solution of 475 mg of the latter product in 5 ml of dimethylformamide was added dropwise under nitrogen to a suspension of 88 mg of sodium hydride as 50% in oil and 7 ml of dimethylformamide under stirring during 45 minutes at the room's temperature and after heating the mixture to 45° C., a solution of 439.9 g of the product of Step L in 4 ml of dimethylformamide was added dropwise. The mixture was stirred at 45° C. for 4 hours and was then cooled and poured into a concentrated, iced monosodium phosphate solution. The mixture was extracted with ethyl acetate and the extracts were washed, dried and evaporated to dryness to obtain 1.14 g of residue which was directly reduced.

A solution of the said 1.14 g of product in 40 ml of ethanol and 4 ml of water was cooled to 0° C. under nitrogen and 135 mg of sodium borohydride were added slowly. The mixture was stirred for an hour at 0° C. and then 0.5 ml of acetone and a concentrated solution of monosodium phosphate were added thereto to adjust the pH to 6. The ethanol was diluted with water and the mixture was extracted with ethyl acetate. The organic extracts were washed with water, reextracted, dried and evaporated to dryness. The residue was chromatographed over silica gel and was eluted with an 85–15 benzene-ethyl acetate mixture containing 0.1% of triethylamine to obtain 76.8 mg of ethyl (8RS, 9SR, 12RS, 15SR) (5Z,13E) 9-acetoxy-15-hydroxy-16-(3'-thienyloxy)-17,18,19,20-tetranor-prosta-5,13-dienoate and 60.5 mg of ethyl (8RS, 9SR, 12RS, 15RS) (5Z, 13E) 9-acetoxy-15-hydroxy-16-(3'-thienyloxy)-17,18,19,20-tetranor-prosta-5,13-dienoate and 62.8 mg of a mixture of the 15SR and 15RS isomers. A second chromatographyl yielded 10 mg of the 15SR isomer and 28.9 mg of the 15RS isomer for a yield of 13.6% of the 15SR isomer and 14% of the 15RS isomer.

STEP N: (8RS, 9SR, 12RS, 15SR) (5Z, 13E) 9,15-dihydroxy-16-(3'-thienyloxy)-17,18,19,20-tetranor-prosta-5, 13-dienoic acid 1 ml of N sodium hydroxide was added dropwise under nitrogen to a solution of 86.8 mg of the 15SR isomer of Step M in 3 ml of ethanol and after 1 hour, 0.5 ml of N sodium hydroxide and 0.5 ml of water were added thereto. The ethanol was evaporated and the residue was taken up in a concentrated monosodium phosphate solution to adjust the pH to 3. The mixture was extracted with ethyl acetate and the extracts were washed and dried to obtain 82 mg of product which was chromatographed over silica gel. Elution with ethyl acetate yielded 65.8 mg of (8RS, 9SR, 12RS, 15SR) (5Z,13E) 9,15-dihydroxy-16-(3'-thienyloxy)17,18,19,20-tetranor-prosta-5,13-dienoic acid.

| UV Spectrum (ethanol): | |
|---|---|
| λ max. = 219 nm | ε = 4900 |
| λ max. = 251 nm | ε = 4100 |
| IR Spectrum (chloroform): | |
| \C=O 1728 and 1715 cm$^{-1}$ / | |
| C=C heterocyclic | 1543 cm$^{-1}$ |
| free OH | 3605 cm$^{-1}$ |
| | 973 cm$^{-1}$ |
| \C=C trans \ | |

EXAMPLE 2

(8RS, 9SR, 12RS, 15RS) (5Z, 13E) 9,15-dihydroxy-16-(3'-thienyloxy)-17,18,19,20-tetranor-prosta-5,13-dienoic acid Using the procedure of Step N in Exampel 1, 89.4 mg of the 15RS isomer of Step M of Example 1 were reacted to obtain 64.7 mg of pure (8RS, 9SR, 12RS, 15RS) (5Z, 13E) 9,15-dihydroxy-16-(3'-thienyloxy)-17,18,19,20-tetranor-prosta-5,13-dienoic acid.

UV Spectrum (ethanol):
λ max. = 219 nm    ε = 4500
λ max. = 251 nm    ε = 3900
IR Spectrum (chloroform):

$>$C$=$O 1743 and 1709 cm$^{-1}$; C$=$C 1543 and 1500 cm$^{-1}$;

free OH 3601 cm$^{-1}$; and C$=$C trans 972 cm$^{-1}$.

EXAMPLE 3

(8RS, 9RS, 12RS, 15SR) (5Z, 13E) 9,15-dihydroxy-16-(3'-thienyloxy)-17,18,19,20-tetranor-prosta-5,13-dienoic acid

STEP A: ethyl (1'RS, 2'RS, 5'SR) (5Z) 7-[2'-hydroxy-5'-(α-tetrahydropyranyloxymethyl)-cyclopentyl]-5-heptenoate and ethyl (1'RS, 2'SR, 5'SR) (5Z) 7-[2'-hydroxy-5'(α-tetrahydropyranyloxymethyl)-cyclopentyl]-5-heptenoate 546 mg of sodium borohydride were added in fractions to a mixture of 3.269 g of the product of Step H of Example 1, 120 ml of ethanol and 12 ml of water at 0° C. and after 2 hours, acetone was added thereto. The pH of the mixture was adjusted to 7 with a monosodium phosphate solution and the mixture was evaporated to dryness. The residue was taken up in water and the aqueous phase was extracted with ethyl acetate to obtain 3.399 g of raw oil. The latter was chromatographed over silica gel and was eluted with a 70–30 cyclohexaneethyl acetate mixture to obtain 0.711 g of ethyl (1'RS, 2'SR, 5'SR) (5Z) 7-[2'-hydroxy-5'-(α-tetrahydropyranyloxymethyl)cyclopentyl]-5-heptenoate identical to that of Step I of Example 1 and 2.053 g of ethyl (1'RS, 2'RS, 5'SR) (5Z) 7-[2'-hydroxy-5'-(α-tetrahydropyranyloxymethyl)-cyclopentyl]-5-heptenoate.

STEP B: ethyl (1'RS, 2'RS, 5'SR) (5Z) 7-[2'-acetoxy-5'-(α-tetrahydropyranyloxymethyl)-cyclopentyl]-5-heptenoate Using the procedure of Step J of Example 1, 2.011 g of the 2'RS isomer of Step A were reacted to obtain without chromatography 2.249 g of ethyl (1'RS, 2'RS, 5'SR) (5Z) 7-[2'-acetoxy-5'-(α-tetrahydropyranyloxymethyl)-cyclopentyl]-5-heptenoate.

STEP C: ethyl (1'RS, 2'RS, 5'SR) (5Z) 7-[2'-acetoxy-5'-hydroxymethyl-cyclopentyl]-5-heptenoate Using the procedure of Step K of Example 1, 1.875 g of the product of Step B were reacted to obtain 1.27 g of ethyl (1'RS, 2'RS, 5'SR) (5Z) 7-[2'-acetoxy-5'-hydroxymethylcyclopentyl]-5-heptenoate.

STEP D: ethyl (1'RS, 2'RS, 5'SR) (5Z) 7-[2'-acetoxy-5'-formyl-1'-cyclopentyl]-5-heptenoate Using the process of Step L of Example 1, 199.5 mg of the product of Step C were reacted to obtain 200 mg of raw ethyl (1'RS, 2'RS, 5'SR) (5Z) 7-[2'-acetoxy-5'-formyl-1'-cyclopentyl]-5-heptenoate which was used as is for the next step.

STEP E: ethyl (8RS, 9RS, 12RS) (5Z, 13E) 9-acetoxy-15-oxo-16-(3'-thienyloxy)-17,18,19,20-tetranor-prosta-5,13-dienoate Using the procedure of Step M of Example 1, an anion was obtained beginning with 212 mg of dimethyl 2-oxo-3-(3'-thienyloxy)-propyl phosphonate and 200 mg of the product of Step D was added thereto dropwise as in Step M of Example 1. The resulting 430 mg of raw product were filtered through florisil and was eluted with an 85–15 benzene-ethyl acetate mixture containing 0.1% of triethylamine to obtain 126.3 mg of ethyl (8RS, 9RS, 12RS) (5Z, 13E) 9-acetoxy-15-oxo-16-(3'-thienyloxy)-17,18,19,20-tetranor-prosta-5,13-dienoate.

STEP F: ethyl (8RS, 9RS, 12RS, 15SR) (5Z, 13E) 9-acetoxy-15-hydroxy-16-(3'-thienyloxy)-17,18,19,20-tetranor-prosta-5,13-dienoate and ethyl (8RS, 9RS, 12RS, 15RS) (5Z, 13E) 9-acetoxy-15-hydroxy-16-(3'-thienyloxy)-17,18,19,20-tetranor-prosta-5,13-dienoate Using the process of Step M of Example 1, 126.3 mg of the product of Step E were treated to obtain 35 mg of ethyl (8RS, 9RS, 12RS, 15SR) (5Z, 13E) 9-acetoxy-15-hydroxy-16-(3'-thienyloxy)-17,18,19,20-tetranor-prosta-5,13-dienoate and 19 mg of ethyl (8RS, 9RS, 12RS, 15RS) (5Z, 13E) 9-acetoxy-15-hydroxy-16-(3'-thienyloxy)-17,18,19,20-tetranor-prosta-5,13-dienoate and 35 mg of a mixture of the 15SR and 15RS isomers. A second chromatography yielded 4.2 mg of the 15SR isomer and 9.6 mg of the 15RS isomer.

STEP G: (8RS, 9RS, 12RS, 15SR) (5Z, 13E) 9,15-dihydroxy-16-(3'-thienyloxy)-17,18,19,20-tetranor-prosta-5,13-dienoic acid Using the procedure of Step N in Example 1, 44.3 mg of the 15SR isomer of Step F were reacted to obtain 31.1 mg of pure (8RS, 9RS, 12RS, 15SR) (5Z, 13E) 9,15-dihydroxy-16-(3'-thienyloxy)-17,18,19,20-tetranor-prosta-5,13-dienoic acid.

IR Spectrum (chloroform):

$>$C$=$O at 1723 and 1709 cm$^{-1}$; C$=$C at 1543 cm$^{-1}$; and OH at 3600 cm$^{-1}$

EXAMPLE 4

(8RS, 9RS, 12RS, 15RS) (5Z, 13E) 9,15-dihydroxy-16-(3'-thienyloxy)-17,18,19,20-tetranor-prosta-5,13-dienoic acid Using the procedure of Step N of Example 1, 44.6mg of the 15 RS isomer of Step F of Example 3 were reacted to obtain 33.5 mg of pure (8RS, 9RS, 12RS, 15RS) (5Z, 13E) 9,15-dihydroxy-16-(3'-thienyloxy)-17,18,19,20-tetranor-prosta-5,13-dienoic acid.

IR Spectrum (chloroform):

>C═O at 1723 and 1709 cm$^{-1}$; C ═ C at 1543 cm$^{-1}$; and OH at 3600 cm$^{-1}$.

EXAMPLE 5

(8RS, 9SR, 12RS, 15SR) (5Z, 13E) 9,15-dihydroxy-16-[4'-(4''-tetrahydropyranyl)-phenoxy]-17,18,19,20-tetranor-prosta-5,13-dienoic acid STEP A: ethyl (8RS, 9SR, 12RS) (5Z, 13E) 9-acetoxy-15-oxo-16-[4'-(4''-tetrahydropyranyl)-phenoxy]-17,18,19,20-tetranor-prosta-5,13-dienoate A suspension of 8.9 g of 4-(4'-tetrahydropyranyl)-phenol in 50 ml of ethanol was added to a mixture of 1.15 g of sodium in 100 ml of anhydrous ethanol which had been prepared one hour earlier and the mixture was stirred for 2 hours at room temperature and was then cooled to 0° C. 6.6 ml of ethyl bromoacetate were added dropwise to the reaction mixture and the mixture was stirred for 2 hours at room temperature and was then refluxed for 2 hours. The mixture was evaporated to dryness and the residue was taken up in ether and water containing 10% of 2N hydrochloric acid. The mixture was decanted and the organic phase was washed with 2N sodium hydroxide, was dried and evaporated to dryness to obtain 14 g of an oil. The latter was chromatographed over silica gel and was eluted with a 90–10 methylene chloride-ethyl acetate mixture to obtain 9.221 g of pure ethyl 4-(4'-tetrahydropyranyl)-phenoxy-acetate.

A solution of 1.876 g of dimethyl methyl-phosphonate in 30 ml of anhydrous tetrahydrofuran was added at −70° C. to 13.8 ml of a 1.1 mole/liter of butyllithium in solution and the mixture was stirred at −70° C. for 2 hours. A solution of 4 g of ethyl 4-(4'-tetrahydropyranyl)-phenoxy-acetate in 40 ml of anhydrous tetrahydrofuran was added to the reaction mixture and the mixture was stirred for 90 minutes at −70° C. The mixture was allowed to return to 0° C. and was hydrolyzed and acidified with monosodium phosphate. The mixture was extracted with ethyl acetate and the extracts were evaporated to dryness to obtain 5.624 g of raw product. The latter was chromatographed over silica gel and was eluted with a 16–4 ethyl acetate-methanol mixture to obtain 3.13 g of pure dimethyl 2-oxo-3-[4'-(4''-tetrahydropyranyl)-phenoxy]-propyl-phosphonate in the form of an oil.

A solution of 126.5 mg of the latter product in 1 ml of glyme was added dropwise under nitrogen to a suspension of 17.5 g of sodium hydride as 50% in oil and 3 ml of anhydrous glyme and the mixture was stirred at room temperature for 90 minutes. A mixture of 77.5 mg of ethyl (1'RS, 2'SR, 5'SR) (5Z) 7-(2'-acetoxy-5'-formyl-1'-cyclopentyl)-5'-heptenoate in 1.5 ml of glyme was added to the reaction mixture and the mixture was rinsed with 1 ml of glyme. The mixture was heated at 50° C. for 8 hours and was then poured into a solution saturated with monosodium phosphate. The mixture was extracted with ethyl acetate and the extracts were washed and dried and evaporated to dryness to obtain 185.4 mg of raw product. The latter was chromatographed over silica gel and was eluted with a 60–40 cyclohexane-ethyl acetate mixture to obtain 63.3 mg of ethyl (8RS, 9SR, 12RS) (5Z, 13E) 9-acetoxy-15-oxo-16-[4'-(4''-tetrahydropyranyl)-phenoxy]-17,18,19,20-tetranor-prosta-5,13-dienoate.

STEP B: ethyl (8RS, 9SR, 12RS, 15SR) (5Z, 13E) 9-acetoxy-15-hydroxy-16-[4'-(4''-tetrahyropyranyl)-phenoxy]-17,18,19,20-tetranor-prosta-5,13-dienoate and ethyl (8RS, 9SR, 12RS, 15RS) (5Z, 13E) 9-acetoxy-15-hydroxy-16-[4'-(4''-tetrahydropyranyl)-phenoxy]-17,18,19,20-tetranor-prosta-5,13-dienoate 7.6 g of sodium borohydride were added in small fractions under nitrogen to a suspension of 14 g of zinc chloride in 225 ml of anhydrous glyme on an ice bath and the mixture was stirred at room temperature for 30 minutes and was filtered under an inert gas. 5 ml of the resulting solution were added at 0° C. under nitrogen to a solution of 291 mg of the product of Step A in 3 ml of glyme and the mixture was allowed to return to room temperature. The mixture was stirred for 4 hours and 0.5 ml of zinc borohydride were added thereto over 3 hours. The mixture was poured into an iced, concentrated monosodium phosphate solution and the mixture was extracted with ethyl acetate. The extracts were washed, dried and evaporated to dryness to obtain 297.5 mg of raw product. The latter was chromatographed over silica gel and was eluted with a 60–40 cyclohexane-ethyl acetate mixture to obtain 60.5 mg of ethyl (8RS, 9SR, 12RS, 15SR) (5Z, 13E) 9-acetoxy-15-hydroxy-16-[4'-(4''-tetrahydropyranyl)-phenoxy]-17,18,19,20-tetranor-prosta-5,13-dienoate and 49.8 g of ethyl (8RS, 9SR, 12RS, 15RS) (5Z,13E)-9-acetoxy-15-hydroxy-16-[4'-(4''-tetrahydropyranyl)-phenoxy]-17,18,19,20-tetranor-prosta-5,13-dienoate and 74.7 mg of a mixture of the 15RS and 15SR isomers. The latter was chromatographed a second time to obtain 21.5 mg of the 15SR isomer and 34.6 mg of the 15RS isomer for a total yield of 82 mg of the 15SR isomer and 84.4 mg of the 15RS isomer.

STEP C: (8RS, 9SR, 15SR) (5Z, 13E) 9,15-dihydroxy-16-[4'-(4''-tetrahydropyranyhl)-phenoxy]-17,18,19,20-tetranor-prosta-5,13-dienoic acid 1 ml of N sodium hydroxide was added under nitrogen at room temperature to a solution of 82 mg of the 15SR isomer of Step B in 2.5 ml of ethanol and 2 ml of water and the mixture was stirred at room temperature for 4½ hours with another 1 ml of N sodium hydroxide being added after the first hour. The ethanol was evaporated and the pH was adjusted to 4 with monosodium phosphate. The mixture was extracted with ethyl acetate and the extracts were washed, dried and evaporated to dryness to obtain 89.5 g of raw product. The latter was chromatographed over silica gel and was eluted with ethyl acetate to obtain 71 mg of pure (8RS, 9SR, 12RS, 15SR)(5Z,13E) 9,15-dihydroxy-16-[4'-(4''-tetrahydropyranyl)phenoxy]-17,18,19,20-tetranor-prosta-5,13-dienoic acid.

IR Spectrum (chloroform):

C═O at 1709 and 1724 cm$^{-1}$; aromatic at 1609, 1582 and 1511 cm$^{-1}$

EXAMPLE 6

(8RS, 9SR, 12RS, 15RS)(5Z,13E) 9,15-dihydroxy-16-[4'-(4''-tetrahydropyranyl)-phenoxy]-17,18,19,20-tetranor-prosta-5,13-dienoic acid A solution of 84.4 mg of the 15RS isomer of Step B of Example 5 in 2.5 ml of ethanol and 1 ml of water were reacted as in step C of Example 5 at room temperature under nitrogen with dropwise addition to obtain 55 mg of pure (8RS, 9SR, 12RS, 15RS)(5Z,13E) 9,15-dihydroxy-16-[4'-(4''-tetrahydropyranyl)-phenoxy]-17,18,19,20-tetranor-prosta-5,13-dienoate with the same IR Spectrum as the product of Step C of Example 5.

EXAMPLE 7

(8RS, 9RS, 12RS, 15SR)(5Z,13E) 9,15-dihydroxy-16-[4'-(4''-tetrahydropyranyl)-phenoxyl]17,18,19,20-tetranor-prosta-5,13-dienoic acid STEP A: ethyl (8RS, 9RS, 12RS)(5Z,13E) 9-acetoxy-15-oxo-16-[4'-(4''-tetrahydropyranyl)-phenoxy]-17,18,19,20-tetranor-prosta-5,13-dienoate A suspension of 108 mg of sodium hydride in 50% oil in 15 ml of glyme was added to a solution of 0.769 mg of dimethyl 2-oxo-3-[4'-(4''-tetrahydropyranyl)-phenoxy]-propylphosphonate in 5 ml of distilled glyme and the mixture was stirred for 90 minutes. A solution of 0.465 g of ethyl (1'RS, 2'RS, 5'SR)(5Z) 7-(2'-acetoxy-5'-formyl-1'-cyclopentyl)-5-heptenoate in 3 ml of glyme were added to the reaction mixture and the mixture was heated at 50° C. for 3½ hours and was then cooled to room temperature. The mixture was hydrolyzed and acidified to a pH of 5 with a saturated monosodium phosphate solution. The mixture was extracted with ethyl acetate and the extracts were evaporated to dryness to obtain 1.12 g of an oil. The oil was chromatographed over silica gel and was eluted with a 6-4 cyclohexane-ethyl acetate mixture to obtain 362 mg of ethyl (8RS, 9RS, 12RS)(5Z,13E) 9-acetoxy-15-oxo-16-[4'-(4''-tetrahydropyranyl)-phenoxy]-17,18,19,20-tetranor-prosta-5,13-dienoate.

STEP B: ethyl (8RS, 9RS, 12RS, 15RS)(5Z,13E) 9-acetoxy-15-hydroxy-16-[4'-(4''-tetrahydropyranyl)-phenoxy]-17,18,19,20-tetranor-prosta-5,13-dienoate and ethyl (8RS, 9RS, 12RS, 15SR) (5Z),13E) 9-acetoxy-15-hydroxy-16-[4'-(4''-tetrahydropyranyl)-phenoxy]-17,18,19,20-tetranor-prosta-5,13-dienoate 7.8 ml of a solution of 0.2 mole/liter of zinc borohydride in glyme were slowly added to a mixture of 300 mg of the product of Step A in 4 ml of redistilled glyme at 0° C. and after returning the mixture to 20° C., the mixture was stirred for an hour and was then slowly poured into a monosodium phosphate solution to obtain a pH of 3. The mixture was extracted with ethyl acetate and the extracts were evaporated to dryness to obtain an oil. The oil was chromatographed over silica gel and was eluted with a 90-10 methylene chloride-ethyl acetate mixture to obtain 159 mg of a mixture of ethyl (8RS, 9RS, 12RS, 15RS)(5Z,13E) 9-acetoxy-15-hydroxy-16-[4'-(4''-tetrahydropyranyl)-phenoxy]-17,18,19,20-tetranor-prosta-5,13-dienoate and ethyl (8RS, 9RS, 12RS, 15SR)(5Z,13E) 9-acetoxy-15-hydroxy-16-[4'-(4''-tetrahydropyranyl)-phenoxyl]-17,18,19,20-tetranor-prosta-5,13-dienoate. After several separations of the mixture on silica gel plates, there were obtained 30 mg of the 15RS isomer with an Rf = 0.32 and 27 mg of the 15SR isomer with Rf = 0.35.

STEP C: (8RS, 9RS, 12RS, 15SR) (5Z,13E) 9,15-dihydroxy-16-[4'-(4''-tetrahydropyranyl)-phenoxy]-17,18,19,20-tetranor-prosta-5,13-dienoic acid 0.4 ml of N sodium hydroxide was added under nitrogen to a solution of 24.8 mg of the 15SR isomer of Step B in 1 ml of ethanol and 1 ml of water and the mixture was stirred for 4½ hours at room temperature. A solution saturated with monosodium phosphate was added to the reaction mixture to adjust the pH to 3 and the mixture was extracted with ethyl acetate. The extracts were washed, dried and evaporated to dryness to obtain 22 mg of pure (8RS, 9RS, 12RS, 15SR)(5Z,13E) 9,15-dihydroxy-16-[4'-(4''-tetrahydropyranyl)-phenoxy]-17,18,19,20-tetranor-prosta-5,13-dienoic acid.

EXAMPLE 8

(8RS, 9RS, 12RS, 15RS)(5Z,13E) 9,15-dihydroxy-16-[4'-(4''-tetrahydropyranyl)-phenoxy]-17,18,19,20-tetranor-prosta-5,13-dienoic acid Using the process of Step C of Example 7, 23.2 mg of the 15RS isomer of Step B of Example 7 were reacted to obtain 20.1 mg of pure (8RS, 9RS, 12RS, 15RS)(5Z,13E) 9,15-dihydroxy-16-[4'-(4''-tetrahydropyranyl)-phenoxy]-17,18,19,20-tetranor-prosta-5,13-dienoic acid.

EXAMPLE 9

(8RS, 9SR, 12RS, 15SR)(5Z,13E) 9,15-dihydroxy-16-thiazolyloxy-17,18,19,20-tetranor-prosta-5,13-dienoic acid STEP A: ethyl 2'-thiazolyloxy-acetate A solution of 5.2 g of ethyl glycolate in 10 ml of dimethylformamide was added over 35 minutes at 0° C. to a suspension of 2.4 g of sodium hydride in 50% oil in 50 ml of dimethylformamide and the mixture was stirred overnight. A solution of 5.05 g of bromothiazole in 10 ml of dimethylformamide was added to the mixture which was then heated at 65° C. for 24 hours and was extracted with ethyl acetate. The extracts were washed, dried and evaporated to dryness at atmospheric pressure to obtain 21.7 g of an oil. The oil was chromatographed over silica gel and was eluted with an 80-20 cyclohexane-ethyl acetate mixture to obtain 3.211 g of ethyl 2'-thiazolyloxy acetate in the form of an oil.

STEP B: dimethyl 2-oxopropyl-3-(2'-thiazolyloxy)-phosphonate

A solution of 13.5 ml of butyllithium in hexane was added dropwise at −70° C. over 30 minutes to a solution of 3.283 g of dimethyl methyl phosphonate in 20 ml of tetrahydrofuran and the mixture was stirred at −70° C. for 1 hour. A solution of 3.283 g of ethyl 2'-thiazolyloxyacetate in 32 ml of tetrahydrofuran was slowly added to the reaction mixture which was then stirred at −70° C. for 3 hours which the temperature returned to 20° C. The reaction mixture was poured into a saturated monosodium phosphate solution and was extracted with ethyl acetate. The extracts were evaporated to dryness to obtain 5.1 g of an oil. The oil was chromatographed over silica gel and was eluted with a 96-4 ethyl acetate-methanol mixture to obtain 2.58 g of dimethyl 2-oxopropyl-3-(2'-thiazolyloxy)-phosphonate in the form of a colorless oil.

STEP C: ethyl (8RS, 9SR, 12RS)(5Z,13E) 9-acetoxy-15-oxo-16-thiazolyloxy-17,18,19,20-tetranor-prosta-5,13-dienoate A solution of 915 mg of the product of Step B in 10 ml of glyme was added dropwise to a suspension of 167 mg of sodium hydride as a 50% oil suspension in 25 ml of glyme and the mixture was stirred at room temperature for 2½ hours. 717 mg of ethyl (1'RS, 2'SR, 5'RS)(5Z) 7-(2'-acetoxy-5'-formyl-1'-cyclopentyl)-5-heptenoate were added thereto and the mixture was heated at 50° C. for 4 hours. The mixture was acidified to a pH of 5 with a saturated monosodium phosphate solution and was extracted with ethyl acetate. The extracts were evaporated to dryness to obtain 1.6 g of an oil. The oil was chromatographed over silica gel and eluted with a 60-40 cyclohexane-ethyl acetate mixture to obtain 0.53 g of ethyl (8RS, 9RS, 12RS)(5Z,13E) 9-acetoxy-15-oxo-16-thiazolyloxy-17,18,19,20-tetranor-prosta-5,13-dienoate.

STEP D: ethyl (8RS, 9SR, 12RS, 15RS)(5Z,13E) 9-acetoxy-15-hydroxy-16-thiazolyloxy-17,18,19,20-tetranor-prosta-5,13-dienoate and ethyl (8RS, 9SR, 12RS)(5Z,13E) 9-acetoxy-15-hydroxy-16-thiazolyloxy-17,18,19,20-tetranor-prosta-5,13-dienoate 7.5 ml of zinc borohydride in glyme (0.2 mole/liter) were added dropwise at 0° C. to a solution of 350 mg of the product of Step C in 7 ml of glyme and after the temperature returned to room temperature, the mixture was stirred for an hour. The pH was adjusted to 5 by addition of a saturated monosodium phosphate solution and the mixture was extracted with ethyl acetate. The extracts were evaporated to dryness to obtain 450 mg of an oil. The oil was chromatographed over silica gel and was eluted with a 60-40 cyclohexane-ethyl acetate mixture to recover a mixture of ethyl (8RS, 9SR, 12RS, 15RS)(5Z,13E) 9-acetoxy-15-hydroxy-16-thiazolyloxy-17,18,19,20-tetranor-prosta-5,13-dienoate and ethyl (8RS, 9SR, 12RS, 15SR)(5Z,13E) 9-acetoxy-15-hydroxy-16-thiazolyloxy-17,18,19,20-tetranor-prosta-5,13-dienoate. Another chromatography over silica gel yielded 68.5 mg of the 15SR isomer, 44.1 mg of the 15RS isomer and 61.8 mg of the mixture which was chromatographed over silica gel again to obtain 15.7 mg of the 15SR isomer and 18.4 mg of the 15RS isomer. This was a total yield of 84.2 mg of the 15SR isomer and 62.5 mg of the 15RS isomer.

STEP E: (8RS, 9SR, 12RS, 15SR)(5Z,13E) 9,15-dihydroxy-16-thiazolyloxy-17,18,19,20-tetranor-prosta-5,13-dienoic acid 1.5 ml of N sodium hydroxide was added under nitrogen to a solution of 84.2 mg of the 15SR isomer of Step D in 2.5 ml of ethanol and 1 ml of water and the mixture was stirred for 5 hours at room temperature. The pH of the mixture was adjusted to 4 with a saturated monosodium phosphate solution and the ethanol was evaporated. The mixture was extracted with ethyl acetate and the extracts were evaporated to dryness to obtain 74.2 mg of raw product. The latter was chromatographed over silica gel and was eluted with ethyl acetate to obtain 40.2 mg of pure (8RS, 9SR, 12RS, 15SR) (5Z,13E) 9,15-dihydroxy-16-thiazolyloxy-17,18,19,20-tetranor-prosta-5,13-dienoic acid.

EXAMPLE 10

(8RS, 9SR, 12RS, 15RS)(5Z,13E) 9,15-dihydroxy-16-thiazolyloxy-17,18,19,20-tetranor-prosta-5,13-dienoic acid Using the procedure of Step E of Example 9, 62.5 mg of the 15RS isomer of Step D of Example 9 were reacted to obtain 36 mg of pure (8RS, 9SR, 12RS, 15RS)(5Z,13E) 9,15-dihydroxy-16-thiazolyloxy-17,18,19,20-tetranor-prosta-5,13-dienoic acid. IR Spectrum (chloroform): OH at 3606 cm$^{-1}$; C=O at 1711 and 1722 cm$^{-1}$ and C=C, CN at 1521 cm$^{-1}$.

EXAMPLE 11

(8RS, 9SR, 12RS, 15RS)(5Z,13E) 9,15-dihydroxy-16-[3'(1'-thia-2',5'-diazolyloxy)]17,18,19,20-tetranor-prosta-5,13-dienoic acid STEP A: 3-methoxy carbethoxy-1,2,5-thiadiazole 19.2 g of sodium hydride in 50% oil were added to a mixture of 40.8 g of 3-hydroxy-1,2,5-thiadiazole in 400 ml of dimethylformamide and the mixture stood at room temperature. A mixture of 83.5mg of ethyl bromoacetate in 80 ml of dimethylformamide was added thereto and the mixture was stirred for 3 hours at room temperature. Water was added and the mixture was extracted with ethyl acetate. The extracts were evaporated to dryness to obtain 78 g of an oil which was distilled to obtain 57 g of 3-methoxy carbethoxy-1,2,5-thiadiazole.

STEP B: dimethyl 2-oxo-3-[3'-(1'-thia-2',5'-diazolyloxy)]-propyl-phosphonate 7.4 ml of a 1.35 mole/liter of butyllithium in hexane were added over 30 minutes at −70° C. to a solution of 1.24 g of methyl methylphosphonate in 12 ml of anhydrous tetrahydrofuran and the mixture was stirred at −70° C. for 2 hours. 1.882 g of the product of Step A was added thereto at −70° C. over one hour and the mixture was stirred at −70° C. for 90 minutes. The temperature returned to 20° C. and the mixture was hydrolyzed and acidified to 5 with a saturated monosodium phosphate solution. The mixture was extracted with ethyl acetate and the extracts were evaporated to obtain 3 g of an oil. The oil was chromatographed over silica gel and was eluted with a 96-4 ethyl acetate-methanol mixture to obtain 1.825 g of pure dimethyl 2-oxo-3-[3'-(1'-thia-2',5'-diazolyloxy)]-propylphosphonate in the form of an oil.

STEP C: ethyl (8RS, 9SR, 12RS)(5Z,13E) 9-acetoxy-15-oxo-16-[3'-(1'-thia-2',5'-diazolyloxy)]-17,18,19,20-tetranor-prosta5,13-dianoate A solution of 745 mg of the product of Step B in 5 ml of glyme was added over 30 minutes to a suspension of 138 mg of sodium hydride in 50% oil in 15 ml of glyme and the mixture was then poured into a solution of 750 mg of ethyl (1'RS, 2'SR, 5'SR)(5Z) 7-(2'-acetoxy-5'-formyl-1'-cyclopentyl)-5-heptenoate in 5 ml of glyme. The mixture was heated at 58° C. for 90 minutes and was then hydrolyzed and acidified to a pH of 5 with a saturated monosodium phosphate solution. The mixture was extracted with ethyl acetate and the extracts were evaporated to obtain 1.366 g of product. The latter was chromatographed over silica gel and was eluted with a 60-40 cyclohexane-ethyl acetate mixture to obtain 720 mg of ethyl (8RS, 9SR, 12RS)(5Z, 13E) 9-acetoxy-15-oxo-16-[3'-(1'-thia-2',5'-diazolyloxy)]-17,18,19,20-tetranor-prosta-5,13-dienoate.

STEP D: ethyl (8RS, 9SR, 12RS, 15RS)(5Z,13E) 9-acetoxy-15-hydroxy-16-[3'-(1'-thia-2',5'-diazolyloxy)]-17,18,19,20-tetranor-prosta-5,13-dienoate and ethyl (8RS, 9SR, 12RS, 15SR) (5Z, 13E) 9-acetoxy-15-hydroxy-16-[3'-(1'-thia-2',5'-diazolyloxy)]-17,18,19,20-tetranor-prosta-5,13-dienoate.

A solution of 690 mg of the product of Step C in 10 ml of glyme cooled to 0° C. was poured into 14 ml of a mixture of 0.22 mole/liter of zinc borohydride in glyme. The temperature returned to room temperature and the mixture was stirred for 75 minutes. The mixture was poured into ice and the pH was adjusted to 5 with a saturated monosodium phosphate solution. The mixture was extracted with ethyl acetate and the extracts were evaporated to obtain 1 g of oil. The oil was chromatographed over silica gel and was eluted with a 70-30 cyclohexane-ethyl acetate mixture to obtain 94 mg of ethyl (8RS, 9SR, 12RS, 15RS)(5Z,13E) 9-acetoxy-15-hydroxy-16-[3'-(1'-thia-2', 5'-diazolyloxy)]-17,18,19,20-tetranor-prosta-5,13-dienoate and 104 mg of ethyl (8RS, 9SR, 12RS, 15SR) (5Z,13E) 9-acetoxy-15-hydroxy-16-[3'-(1'-thia-2',5'-diazolyloxy)]-17,18,19,20-tetranor-prosta-5,13-dienoate.

STEP E: (8RS, 9SR, 12RS, 15RS)(5Z,13E) 9,15-dihydroxy-16-[3'-(1'-thia-2',5'-diazolyloxy)]17,18,19,20-tetranor-prosta-5,13-dienoic acid A mixture of 94 mg of the 15RS isomer of Step D, 2 ml of ethanol, 3.4 ml of water and 1.6 ml of N sodium hydroxide was stirred at room temperature for 8 hours and was evaporated under reduced pressure. The pH was adjusted to 5 with a saturated monosodium phosphate solution and the mixture was extracted with ethyl acetate. The extracts were evaporated to obtain 75 ml of an oil. The oil was chromatographed over silica gel and was eluted with ethyl acetate to obtain 35 mg of (8RS, 9SR, 12RS, 15RS)(5Z,13E) 9,15-dihydroxy-16-[3'-(1'-thia-2',5'-diazolyloxy)]-17,18,19,20-tetranor-prosta-5,13-dienoic acid.

IR Spectrum (chloroform): C=O at 1711 $cm^{-1}$; C=C at 1621 $cm^{-1}$; C=N heterocyclic 1515$cm^{-1}$; and OH at 3606 and 3580 $cm^{-1}$.

EXAMPLE 12

(8RS, 9SR, 12RS, 15SR)(5Z,13E) 9,15-dihydroxy-16-[3'-(1'-thia-2',5'-diazolyloxy)]-17,18,19,20-tetranor-prosta-5,13-dienoic acid Using the procedure of Step E of Example 11, 104 mg of the 15SR isomer of Step D of Example 11 were reacted to obtain (8RS, 9SR, 12RS, 15SR)(5Z,13E) 9,15dihydroxy-16-[3'-(1'-thia-2',5'-diazolyloxy)]-17,18,19,20-tetranor-prosta-5,13-dienoic acid.

EXAMPLE 13

(8RS, 9SR, 12RS, 15RS, 16RS, 16SR)(5Z,13E) 9,15-dihydroxy-16-[4'-(4''-tetrahydroxypyranyl)-phenoxy[-18,19,20,-trinor-prosta-5,13-dienoic acid STEP A: ethyl 2-[4'-(4''-tetrahydropyranyl)-phenoxy]-propanoate A suspension of 8.9 g of 4-(p-hydroxyphenyl)-tetrahydropyran in 50 ml of ethanol was added to a mixture of 1.15 g of sodium in 100ml of ethanol and the mixture was stirred at room temperature for 2 hours. The mixture was cooled to 0° C. and 7.82 ml of ethyl 2-bromopropanoate were added thereto. The mixture returned to room temperature and the mixture was refluxed for 5 hours. The mixture was evaporated to dryness and the residue was taken up in a mixture of 100 ml of ether, 45 ml of water and 5 ml of 2N hydrochloric acid. The aqueous phase was decanted and the organic phase was washed with 2N sodium hydroxide solution, was dried and evaporated to dryness under reduced pressure to obtain 7.9 g of ethyl 2-[4'-(4''-tetrahydropyranyl)-phenoxy]-propanoate with a boiling point of 138°-140° C. at 0.05 mm Hg.

STEP B: dimethyl 2-oxo-3-[4''-(4'''-tetrahydropyranyl)-phenoxy]-butyl phosphonate 11 ml of a 1.8 moles/liter solution of butyllithium in hexane were added at −70° C. to a solution of 2.481 g of dimethyl methyl phosphonate in 5 ml of tetrahydrofuran and the mixture was stirred for 2 hours at −70° C. A solution of 5.6 g of the product of Step A in 20 ml of tetrahydrofuran was added over 20 minutes and the mixture was stirred at −70° C. for 1 hour. After the temperature returned to room temperature, the mixture was hydrolyzed and acidified to a pH of 5 with a saturated monosodium phosphate solution. The mixture was extracted with ethyl acetate and the extracts were evaporated to dryness to obtain 8.27 g of raw oil. The oil was chromatographed over silica gel and was eluted with a 96-4 ethyl acetate-methanol mixture to obtain 3.35 g of dimethyl 2-oxo-3-[4'-(4''-tetrahydropyranyl)-phenoxy]-butyl phosphonate.

STEP C: ethyl (8RS, 9SR, 12RS, 16RS, 16SR)(5Z,13E) 9-acetoxy-15-oxo-16-[4'-(4''-tetrahydropyranyl)-phenoxy]-18,19,20-trinor-prosta-5,13-dienoate A solution of 1.02 g of the product of Step B in 10 ml of dimethylformamide was added dropwise under nitrogen to a mixture of 138 mg of sodium hydride in 50% oil and 11 ml of dimethylformamide and the mixture was stirred for 20 minutes at room temperature. A solution of 745 mg of ethyl (1'RS, 2'SR, 5'SR)(5Z) 7-(2'-acetoxy-5'-formyl-1'-cyclopentyl)-5-heptenoate in 8 ml of dimethylformamide was added dropwise under nitrogen to the mixture which was then heated at 50° C. for 4 hours and stood overnight at room temperature. The mixture was poured into a saturated monosodium phosphate solution and was extracted with ethyl acetate. The extracts were evaporated to dryness to obtain 1.743 g of raw product which was chromatographed over silica gel. Elution with an 80-20 benzene-ethyl acetate mixture yielded 178 mg of pure ethyl (8RS, 9SR, 12RS, 16RS, 16SR)(5Z,13E) 9-acetoxy-15-oxo-16-[4'-(4''-tetrahydropyranyl)-phenoxy]-18,19,20-trianor-prosta-5,13-dienoate.

STEP D: ethyl (8RS, 9SR, 12RS, 15RS, and 15SR, 16RS, 16SR) (5Z,13E)-9-acetoxy-15-hydroxy-16-[4'-(4''-tetrahydropyranyl)-phenoxy]-18,19,20-trinor-prosta-5,13-dienoate 4.8 ml of a mixture of 0.22 mole/liter of zinc borohydride in glyme were added at 0° C. to a solution of 170 mg of the product of Step C in 3 ml of glyme and after the temperature returned to room temperature, the mixture was stirred for 90 minutes. The mixture was poured into a saturated monosodium phosphate solution to obtain a pH of 5. The mixture was extracted with ethyl acetate and the extracts were evaporated to dryness to obtain 213 mg of raw product. The latter was chromatographed over silica gel and was eluted with an 80-20 benzene-ethyl acetate mixture to obtain 34 mg of ethyl (8RS, 9SR, 12RS, 15SR, 16RS, 16SR)(5Z,13E) 9-acetoxy-15-hydroxy-16-[4'-(4''-tetrahydropyranyl)-phenoxyl]-18,19,20-trinor-prosta-5,13-dienoate and 38 mg of ethyl (8RS, 9SR, 12RS, 15RS, 16RS, 16SR)(5Z,13E) 9-acetoxy-15-hydroxy-16-[4'-(4''-tetrahydropyranyl)-phenoxy]-18,19,20-trinor-prosta-5,13-dienoate.

STEP E: (8RS, 9SR, 12RS, 15RS, 16RS, 16SR)(5Z13E) 9,15-dihydroxy-16-[4'-(4''-tetrahydropyranyl)-phenoxy]-18,19,20-trinor-prosta-5,13-dienoic acid 0.28 ml of N sodium hydroxide was added under nitrogen to a solution of 38 mg of the 15RS isomer of Step D in 1 ml of ethanol containing 0.1 ml of water and the mixture was stirred for 6½ hours at room temperature. The mixture was evaporated to dryness and the residue was taken up in a water-ethyl acetate mixture saturated with monosodium phosphate and the mixture was extracted with ethyl acetate. The extracts were evaporated to dryness to obtain 51 mg of raw product. The latter was chromatographed over silica gel and was eluted with ethyl acetate to obtain 15 mg of pure (8RS, 9SR, 12RS, 15RS, 16RS, 16SR)(5Z,13E) 9,15-dihydroxy-16-[4'-(4''-tetrahydropyranyl)-phenoxy]-18,19,20-trinor-prosta-5,13-dienoic acid.

EXAMPLE 14 (8RS, 9SR, 12RS, 15SR, 16RS, 16SR)(5Z,13E)
9,15-dihydroxy-16-[4'-(4''-tetrahydropyranyl)-phenoxyl-18,19,20-trinor-prosta-5,13-dienoic acid Using the procedure of Step E of Example 13, 34 mg of the 15SR isomer of Step D of Example 13 were reacted to obtain (8RS, 9SR, 12RS, 15SR, 16 RS, 16SR)(5Z,13E) 9,15-dihydroxy-16-[4'-(4''-tetrahydropyranyl)-phenoxy]-18,19,20-trinor-prosta-5,13-dienoic acid.

EXAMPLE 15

Tris(hydroxymethyl)-methylamine salt of (8RS, 9SR, 12RS, 15RS) (5Z,13E) 9,15-dihydroxy-16-(3'-thienyloxy)-17,18,19,20-tetranor-prosta-5,13-dienoic acid 35.7 mg of the acid of Example 2 and 11.4 mg of tris (hydroxymethyl)-aminomethane were dissolved in 1 ml of methanol and 1 ml of water and the mixture stood for 30 minutes. The mixture was evaporated to dryness to obtain 47.1 g of the tris(hydroxymethyl)-methylamine salt of (8RS, 9SR, 12RS, 15RS)(5Z,13E) 9,15-dihydroxy-16-(3'-thienyloxy)-17,18,19,20-tetranor-prosta-5,13-dienoic acid. The same procedure was repeated for the acids of other examples with the results reported in Table I.

TABLE I

| Acid of Example | Mg of acid | Mg of base |
|---|---|---|
| 1 | 36.7 | 11.7 |
| 4 | 33.5 | 10.6 |
| 3 | 31.1 | 9.9 |
| 6 | 23.7 | 6.2 |
| 5 | 25.2 | 6.65 |
| 10 | 28 | 8.9 |
| 13 | 15 | 3.8 |

EXAMPLE 16

(8RS, 9SR, 12RS, 15RS)(5Z,13E) 9,15-dihydroxy-16-[3'-(5'-chloro)-thienyloxy]-17,18,19,20-tetranor-prosta-5,13-dienoic acid STEP A: 2-ethoxycarbonyl-3-hydroxy-5-chlorothiophene A solution of 23.6 mm of the sodium salt of ethyl thioglycolate in 100 ml of ethanol was added over 5 minutes at 30° C. to a a mixture of 4 g of ethyl dichloroacrylate in 50 ml of ethanol and the mixture was stirred at 25°–30° C. for 15 minutes and was then returned to room temperature. A mixture of 3.22 g of sodium ethylate in 75 ml of ethanol was added thereto and the mixture was stirred for 18 hours. The mixture was concentrated and poured into water and the mixture was extracted with ether. The aqueous phase was acidified with hydrochloric acid and was extracted with ether. The ether phase was evaporated to dryness and the 4.2 g of residue was chromatographed over silica gel. Elution with benzene yielded 1.75 g of 2-ethoxycarbonyl-3-hydroxy-5-chloro-thiophene with Rf = 0.4–0.5.

STEP B: ethyl (2-ethoxycarbonyl-5-chloro-3-thienyl)-oxyacetate 1.07 g of potassium carbonate and 1.3 g of ethyl bromoacetate were added to a solution of 1.6 g of the product of Step A in 50 ml of methyl ethyl ketone and the mixture was refluxed for an hour and was cooled to 30° C. The mixture was filtered and the filtrate was evaporated to dryness. The residue was taken up in ethyl acetate and the solution was washed with water, dried and evaporated to dryness to obtain 2.3 g of ethyl (2-ethoxycarbonyl-5-chloro-3-thienyl)-oxyacetate.

STEP C: (2-carboxy-5-chloro-3-thienyl)-oxyacetic acid

A mixture of 2.26 g of the product of Step B and 40 ml of 2N sodium hydroxide was refluxed under nitrogen for 45 minutes and the mixture was cooled to 20° C. 12 ml of 10N hydrochloric acid were added thereto and the mixture was vacuum filtered. The precipitate was washed twice with iced water to obtain 1.66 g of (2-carboxy-5-chloro-3-thienyl)oxyacetic acid melting at 214° C.

STEP D: 2-chloro-4-thienyloxy-acetic acid

A mixture of 1.63 g of the product of Step C, 3.5 ml of quinoline and 0.24 g of Gattermann copper was heated to 200° C. under nitrogen during which 165 ml of carbon dioxide gas evolved for the water and the mixture was then poured into iced water. 5.6 ml of 10N hydrochloric acid were added thereto and the mixture was extracted with ether. The ether phase was dried and evaporated to dryness and the residue was effloresced with petroleum ether (Bp −60°–80° C.) to obtain 1.2 g of 2-chloro-4-thienyloxy-acetic acid melting at 119° C.

STEP E: methyl 2-chloro-4-thienyloxy-acetate 20 ml of N diazomethane in methylene chloride were added at 0° C. over 5 minutes to a solution of 1.1 g of the product of Step A in 30 ml of methylene chloride and after standing at 0° C. for 15 minutes, the mixture was evaporated to dryness to obtain 1.2 g of methyl 2-chloro-4-thienyloxyacetate.

STEP F: methyl 2-oxo-3-(2-chloro-4-thienyloxy)-propyl phosphonate 4.53 ml of 1.6N butyllithium in hexane were added at −63° C. over one hour under nitrogen to a solution of 0.9 g of methyl methylphosphonate in 30 ml of tetrahydrofuran and the mixture was stirred at −63° C. for an hour. A mixture of 1.2g of the product of Step E in 25 ml of tetrahydrofuran was added to the mixture and the temperature was permitted to return to 10° C. The mixture was poured into a mixture of 50 ml of water and 50 ml of monosodium phosphate and was extracted with ethyl acetate. The extracts were dried and evaporated to dryness to obtain 2.2 g of an oil. The oil was chromatographed over silica gel and was eluted with ethyl acetate to obtain 1.094 g of methyl 2-oxo-3-(2-chloro-4-thienyloxy)-propyl phosphonate with a Rf = 0.2.

STEP G: ethyl (8RS, 9SR, 12RS)(5Z,13E) 9-acetoxy-15-oxo-16-[3'-(5'-chloro)-thienyloxy]-17,18,19,20-tetranor-prosta-5,13-dienoate 170 mg of sodium hydride in 50% oil were added over 5 minutes to a mixture of 1.017 g of the product of Step F in 15 ml of dimethoxy ethane and the mixture stood at room temperature for 45 minutes. The mixture was heated to 50° C. and a mixture of 1.5 g of ethyl (1'RS, 2'SR, 5'SR)(5Z) 7-(2'-acetoxy-5'-formyl-1'-cyclopentyl)-5-heptenoate in 15 ml of dimethoxy ethane was added thereto. The mixture was held at 50° C. for 3 hours and was then evaporated to dryness. The residue was taken up in ether and the solution was acidified with 50 ml of water and 25 ml of 100 g/l of monosodium phosphate in water. The mixture was decanted and the aqueous phase was extracted with ethyl acetate. The extracts were dried and evaporated to dryness to obtain 2 g of an oil which was chromatographed over silica gel. Elution with an 85-15 benzene-ethyl acetate mixture yielded 0.437 g of ethyl (8RS, 9SR, 12RS)(5Z,13E) 9-acetoxy-15-oxo-16-[3'-(5-chloro)-thienyloxy]-17,18,19,20-tetranor-prosta-5,13-dienoate in the form of an oil.

STEP H: ethyl (8RS, 9SR, 12RS, 15RS)(5Z,13E) 9-acetoxy-15-hydroxy-16-[3'-chloro)-thienyloxy]-17,18,19,20-tetranor-prosta-5,13-dienoate and ethyl (8RS, 9SR, 12RS, 15SR)(5Z,13E)-9-acetoxy-15-hydroxy-16-[3'-(5'-chloro)-thienyloxy]-17,18,19,20-tetranor-prosta-5,13-dienoate 5.9 ml of a solution of 0.4N zinc borohydride in dimethoxyethane were added dropwise at 20°-25° C. under nitrogen to a mixture of 0.426 g of the product of G in 5 ml of dimethoxyethane and the mixture was stirred for an hour at room temperature 20 ml of acetone were added thereto and the mixture was evaporated to dryness. The residue was taken up in 50 ml of saturated monosodium phosphate and 50 ml of water and was extracted with ether. The extracts were evaporated to obtain 449mg of product which was chromatographed over silica gel. Elution with an 85-15 benzene-ethyl acetate mixture yielded 93 mg of ethyl (8RS, 9SR, 12RS, 15RS)(5Z,13E)-9-acetoxy-15-hydroxy -16-[3'-(5'-chloro)-thienyloxy]-17,18,19,20-tetranor-prosta-5,13-dienoate and 90 mg of ethyl (8RS, 9SR, 21Rs, 15SR)(5Z,13E) 9-acetoxy-15-hydroxy-16-[3'-(5'-chloro)thienyloxy]-17,18,19,20-tetranor-prosta-5,13-dienoate.

STEP I: (8RS, 9SR, 12RS, 15RS)(5Z,13E) 9,15-dihydroxy-16-[3'-(5'chloro)-thienyloxy)-17,18,19,20-tetranor-prosta-5,13-dienoic acid 3 ml of N sodium hydroxide were added to a solution of 93 mg of the 15 RS isomer of Step H in 2 ml of ethanol and 2 ml of water and the mixture was heated at 45° C. for 4 hours. The ethanol was evaporated under reduced pressure and the mixture was acidified with 11 ml of a solution of 100 g/liter of monosodium phosphate solution. The mixture was extracted with ether and the extracts were dried and evaporated to dryness to obtain 84 mg of an oil. The oil was chromatographed over silica gel and was eluted with ethyl acetate to obtain 47 mg of (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid with an Rf = 0.25.

EXAMPLE 17

(8RS, 9SR, 12RS, 15SR)(5Z,13E) 9,15-dihydroxy-16-[3'-(5'-chloro)-thienyloxy]-17,18,19,20-tetranor-prosta-5,13-dienoic acid Using the procedure of Step I of Example 16, 90 mg of the 15SR isomer of Step H of Example 16 were reacted to obtain 47 mg of (8RS, 9SR, 12RS, 15SR)(5Z,13E) 9,15-dihydroxy-16-[3'-(5'-chloro)-thienyloxy]-17,18,19,20-tetranor-prosta-5,13-dienoic acid.

EXAMPLE 18

8RS, 9SR, 12RS, 15RS)(5Z,13E) 9,15-dihydroxy-16-[3'-(2'-chloro)-thienyloxy]-17,18,19,20-tetranor-prosta-5,13-dienoic acid STEP A: 2-chloro-3-thienyloxy-acetic acid A mixture of 4.8 g of 3-thienyloxy-acetic acid, 50 ml of carbon tetrachloride and 28 ml of sulfonyl chloride was refluxed for an hour and activated carbon was added. The mixture was filtered hot and the filtrate was evaporated to dryness to obtain 5.3 g of 2-chloro-thienyloxy acetic acid melting at 85° C.

STEP B: methyl 2-chloro-thienyloxy-acetate

A mixture of 1.93 g of the product of Step A, 25 ml of methanol, 0.75 g of potassium methylate and 25 ml of methyl iodide was refluxed for 24 hours and was then evaporated to dryness. The residue was taken up in ether and the ether phase was washed with dilute sodium bicarbonate, dried, treated with activated carbon and was filtered. The filtrate was evaporated to dryness to obtain 1.79 g of methyl-2-chloro-thienyloxy-acetate.

STEP C: methyl 2-oxo-3-(2-chloro-3-thienyloxy)-propyl phosphonate 6.2 ml of a solution of 1.3N butyllithium in hexane were added dropwise at −50° C. under nitrogen to a mixture of 0.992 g of methyl methylphosphonate in 5 ml of tetrahydrofuran and then a mixture of 1.64 g of the product of Step B in 5ml of tetrahydrofuran was added thereto at −50° C. The mixture was stirred for 30 minutes at −50° C. and the temperature was allowed to rise to −20° C. The mixture was poured in 50 ml of 100 g/l of monosodium phosphate solution and the mixture was extracted with ether. The ether extracts were dried, filtered and evaporated to dryness to obtain 2.1 g of an oil. The oil was chromatographed over silica gel and was eluted with ethyl acetate to obtain 1.59 g of methyl 2-oxo-3-(2-chloro-3-thienyloxy)-propylphosphonate.

STEP D: ethyl (8RS, 9SR, 12RS) (5Z,13E) 9-acetoxy-15-oxo-16-[3'-(2'-chloro)-thienyloxy]-17,18,19,20-tetranor-prosta-5,13-dienoate 160 mg of sodium hydride in 50% oil were added to a mixture of 954 mg of the product of Step C and 5 ml of dimethoxyethane and the mixture was held at 30° C. for 15 minutes. 3.2 mm of ethyl (1'RS, 2'SR, 5'SR)(5Z) 7-(2'-acetoxy-5'-formyl-1'-cyclopentyl)-5-heptenoate in 5 ml of dimethoxyethane were added thereto and the mixture was heated at 65° C. for 2½ hours. The mixture was evaporated to dryness and the residue was taken up in ether and 50 ml of a solution of 50 g/l of monosodium phosphate were added thereto. The organic phase was decanted, washed with water, dried and evaporated to dryness to obtain 1.5 ml of a brown oil. The oil was chromatographed over silica gel and was eluted with an 85-15 benzene-ethyl acetate mixture to obtain 686 mg of ethyl (8RS, 9SR, 12RS)(5Z,13E) 9-acetoxy-15-oxo-16-[3'-(2'-chloro)-thienyloxy]-17,18,19,20-tetranor-prosta-5,13-dienoate in the form of a clear oil.

STEP E: ethyl (8RS, 9SR, 12RS, 15RS)(5Z,13E) 9-acetoxy-15-hydroxy-16-[3'-(2'-chloro)-thienyloxy]-17,18,19,20-tetranor-prosta-5,13-dienoate and ethyl (8RS, 9SR, 12RS, 15SR)(5Z,13E)-9-acetoxy-15-hydroxy-16-[3'-(2'-chloro)-thienyloxy]-17,18,19,20-tetranor-prosta-5,13-dienoate 8 ml of 0.4N zinc borohydride in dimethoxyethane were added at room temperature under nitrogen to a mixture of 620 mg of the product of Step D in 5 ml of dimethoxyethane and the mixture was stirred at room temperature for 3 hours. The mixture was poured into 20 ml of a 10% monosodium phosphate aqueous solution and the mixture was extracted 3 times with ether. The extracts were dried, filtered and evaporated to dryness to obtain 710 mg of a yellow oil. The oil was chromatographed over silica gel and elution with an 85-15 benzene-ethyl acetate mixture yielded 108 mg of ethyl (8RS, 9SR, 12RS, 15RS)(5Z,13E) 9-acetoxy-15-hydroxy-16-[3'-(2'-chloro)-thienyloxy]-17,18,19,20-tetranor-prosta-5,13-dienoate and 80 mg of ethyl (8RS, 9SR, 12RS, 15SR)(5Z,13E) 9-acetoxy-15-hydroxy-16-[3'-(2'-chloro)-thienyloxy]-17,18,19,20-tetranor-prosta-5,13-dienoate.

STEP F: (8RS, 9RS, 15RS)(5Z,13E) 9,15-dihydroxy-16-[3'-(2'-chloro)-thienyloxy]-17,18,19,20-tetranor-prosta-5,13-dienoic acid A mixture of 108 mg of the 15RS isomer of Step E, 1 ml of methanol and 1 ml of N sodium hydroxide was stirred at room temperature for 2 hours and after the addition of 2 more ml of N sodium hydroxide, the mixture was stirred for 3 hours. The ethanol was evaporated under reduced pressure and 3 ml of N hydrochloric acid and 5 ml of water were added thereto. The mixture was extracted with ether and the ether extracts were dried, filtered and evaporated to dryness to obtain 101 mg of an oil. The oil was chromatographed over silica gel and was eluted with ethyl acetate to obtain 101 mg of (8RS, 9SR, 12RS, 15RS)(5Z,13E) 9,15-dihydroxy-16-[3'-(2'-chloro)-thienyloxy]-17,18,19,20-tetranor-prosta-5,13-dienoic acid with an Rf = 0.2.

EXAMPLE 19

(8RS, 9SR, 12RS, 15RS)(5Z,13E) 9,15-dihydroxy-16-[3'-(4'-chloro)-thienyloxy]-17,18,19,20-tetranor-prosta-5,13-dienoic acid STEP A: 2,4-dichloro-2-methoxycarbonyl-3-oxo-2,3-dihydrothiophene 66.77 g of N-chlorosuccinimide were added to a solution of 31.63 g of 2-methoxycarbonyl-3-hydroxy-thiophene in 150 ml of acetic acid and the mixture was held at 85° C. for 4 hours. The mixture was cooled and was poured into 500 ml of iced water. The mixture was extracted with ether and the ether extracts were washed with potassium bicarbonate solution and dried to obtain an oil which crystallized with a melting pointof <50° C. which was 2,4-dichloro-2-methoxycarbonyl-3-oxo-2,3-dihydrothiophene.

STEP B: 2-methoxycarbonyl-3-hydroxy-4-chloro-thiophene

A solution of 34 g of the product of Step A in 100 ml of ether was added dropwise to a mixture of 10.78 g of powdered zinc in 30 ml of anhydrous ether and a crystal of iodine and and the mixture was refluxed for 5 hours. 100 ml of ether were added thereto and the mixture was added to 100 ml of 10N hydrochloric acid in one liter of water. The mixture was stirred for 30 minutes and was extracted with ethyl acetate. The extracts were passed through a sodium salt soluble in water and the aqueous solution was acidified and extracted with ether. The ether extracts were dried and evaporated to dryness to obtain 19 g of an oil. The oil was chromatographed over silica gel and was eluted to obtain 13 g of 2-methoxycarbonyl-3-hydroxy-4-chloro-thiophene melting at 78° C.

STEP C: ethyl [3-(2-methoxycarbonyl-4-chloro)-thienyl]-oxyacetate 2.16 g of anhydrous potassium carbonate and 2.6 g of ethyl bromoacetate were added to a solution of 3 g of the product of Step B in 150 ml of acetone and 25 ml of methyl ethyl ketone and the mixture was refluxed with stirring for 4 hours. The mixture was cooled to room temperature and was filtered. The acetone was evaporated and the oily residue was taken up in 100 ml of ethyl acetate. The mixture was washed with dilute sodium hydroxide and then with water, was dried and evaporated to dryness. The crystalline product was effloresced with petroleum ether (B.p. = 60°-80° C.) to obtain 3.4 g of ethyl [3-(2-methoxycarbonyl-4-chloro)-thienyl]-oxyacetate melting at 58° C.

STEP D: [3-(2-carboxy-4-chloro)-thienyl]-oxyacetic acid

A mixture of 11.2 g of the product of Step C and 200ml of 2N sodium hydroxide solution was refluxed for 45 minutes and was then cooled and acidified with 60 ml of 12N hydrochloric acid. The mixture was vacuum filtered and the product was washed with iced water and dried to obtain 9.1 gof [3-(2-carboxy-4-chloro)-thienyl]-oxyacetic acid melting at 198° C.

STEP E: 4-chloro-3-thienyl-oxyacetic acid

A mixture of 17.3 ml of quinoline, 8 g of the product of Step E and 1.2 g of Gattermann copper was heated under nitrogen at 200° C. on a metallic bath during which 720 ml of carbon dioxide rapidly evolved and after 15 minutes, the mixture was poured into ground ice containing 28 ml of 10N hydrochloric acid. The mixture was extracted with ether and the extracts were dried and evaporated to dryness to obtain 6.5 g of an oil which solidified. The product was effloresced with petroleum ether (B.p. = 40°-70° C.) to obtain 5 g of 4-chloro-3-thienyl-oxyacetic acid melting at 123° C.

STEP F: methyl 4-chloro-3-thienyl oxyacetate 200 ml of a solution of N/5diazomethane in methylene chloride were added at 0° C. over 15 minutes to a mixture of 5 g of the product of Step E in 50 ml of methylene chloride and the mixture stood at room temperature for one hour. The mixture was evaporated to dryness at 40° C. under reduced pressure to obtain 5.7 g of an oil. The oil was chromatographed over silica gel and was eluted with an 8-2 -cyclohexane ethyl acetate mixture to obtain 3.8 g of methyl 4-chloro-3-thienyloxy acetate with an Rf = 0.35.

STEP G: methyl 2-oxo-3-(3-chloro-4-thienyloxy)-propyl phosphonate 13.77 ml of a 1.3M butyllithium solution in hexane were added over one hour to a mixture of 1.93 ml of dimethyl methyl phosphonate in 35 ml of anhydrous tetrahydrofuran at −65° C. and 40 ml of tetrahydrofuran were added thereto. The mixture was stirred for 45 minutes and then a solution of 3.7 g of the product of Step F in 40 ml of tetrahydrofuran was added. The mixture was held at −65° C. for one hour and was then concentrated and poured into 50 ml of a dilute monosodium phosphate solution. The mixture was extracted with ethyl acetate and the extracts were dried and evaporated to dryness. The residue was chromatographed over silica gel and was eluted with ethyl acetate to obtain 2.2 g of methyl 2-oxo-3-(3-chloro-4-thienyloxy)-propyl phosphonate with an Rf = 0.25.

STEP H: ethyl (8RS, 9SR, 12RS)(5Z,13E) 9-acetoxy-15-oxo-16-[3'-(4'-chloro)-thienyloxy]-17,18,19,20-tetranor-prosta-5,13-dienoate 285 mg of sodium hydride in 51% oil were added under nitrogen to a mixture of 1.704 g of the product of Step G in 15 ml of dimethoxyethane and the mixture stood at room temperature for 45 minutes. A mixture of 1.8 g of ethyl (1'RS, 2'SR, 5'SR)(5Z) 7-(2'-acetoxy-5'-formyl-1'-cyclopentyl)-5-heptenoate in 15 ml of dimethoxyethane was added thereto and the mixture was heated at 60° C. for 3 hours. The mixture was evaporated to dryness and the residue was taken up in ether. The ether phase was poured into monosodium phosphate solution and the mixture was decanted. The aqueous phase was extracted with ethyl acetate and the organic phase was washed with water, dried and evaporated to dryness to obtain 3.4 g of an oil. The oil was chromatographed over silica gel and was eluted with a 9-1 benzene-ethyl acetate mixture to obtain 1.18 g of ethyl (8RS, 9SR, 12RS) (5Z,13E) 9-acetoxy-15-oxo-16-[3'-(4'-chloro)-thienyloxy]-17,18,19,20-tetranor-prosta-5,13-dienoate in the form of a clear oil with an Rf = 0.4.

STEP I: ethyl (8RS, 9SR, 12RS, 15RS)(5Z,13E) 9-acetoxy-15-hydroxy-16-[3'-(4'-chloro)-thienyloxy]-17,18,19,20-tetranor-prosta-5,13-dienoate and ethyl (8RS, 9SR, 12RS, 15SR)(5Z,13E)-9-acetoxy-15-hydroxy-16-[3'-(4'-chloro(-thienyloxy]-17,18,19,20-tetranor-prosta-5,13-dienoate 16 ml of a solution of 0.4N zinc borohydride in dimethoxyethane were added dropwise under nitrogen to a mixture of 1.16 g of the product of Step H in 10 ml of dimethoxymethane and the mixture was stirred for 90 minutes at room temperature. 20 ml of acetone were added thereto and the mixture was evaporated to dryness. The residue was taken up in ether and the ether phase was washed with an acid solution, extracted and evaporated to dryness to obtain 1.2 g of a mixture of 2 isomers. The product was chromatographed over silica gel and was eluted with a 85-15 benzene-ethyl acetate mixture to obtain 240 mg of ethyl (8RS, 9SR, 12RS, 15RS)(5Z,13E) 9-acetoxy-15-hydroxy-16-[3'-(4'-chloro)-thienyloxy]-17,18,19,20-tetranor-prosta-5,13-dienoate and 154 mg of ethyl (8RS, 9SR, 12RS, 15SR)(5Z,13E) 9-acetoxy-15-hydroxy-16-[3'-(4'-chloro)-thienyloxy]-17,18,19,20-tetranor-prosta-5,13-dienoate.

STEP J: (8RS, 9SR, 12RS, 15RS)(5Z,13E) 9,15-dihydroxy-16-[3'-(4'-chloro)-thienyloxy]-17,18,19,20-tetranor-prosta-5,13-dienoic acid 5 ml of water and 2 ml of N sodium hydroxide were added to a solution of 230 ml of the 15RS isomer of Step I in 5 ml of ethanol and the mixture was stirred for 3 hours at 40° to 50° C. The ethanol was evaporated under reduced pressure and 25 ml of a solution of 100 g/liter of monosodium phosphate were added thereto. The mixture was extracted with ether and the ether extracts were dried and concentrated to dryness to obtain 300 mg of a clear oil. The oil was chromatographed over silica gel and was eluted with ethyl acetate to obtain 155 mg of (8RS, 9SR, 12RS, 15RS)(5Z,13E) 9,15-dihydroxy-16-[3'-(4'-chloro)-thienyloxy]-17,18,19,20-tetranor-prosta-5,13-dienoic acid.

EXAMPLE 20

(8RS, 9SR, 12RS, 15RS)(5Z,13E) 9,15-dihydroxy-16-[3'-(2'-cyano-5'-methyl)-thienyloxy]-17,18,19,20-tetranor-prosta-5,13-dienoic acid

STEP A: ethyl (2-cyano-5-methyl-3-thienyl)-oxyacetate 7.2 g of potassium methylate were added to a solution of 13.9 g of 2-cyano-3-hydroxy-5-methyl-thiophene in 150 ml of anhydrous methanol and was evaporated to dryness. The product was washed three times with ether and was dried to obtain 19.5 g of salt which was added to 50 ml of dimethylformamide. 11.13 ml of ethyl bromoacetate were added dropwise thereto and the mixture stood at 50° C. for 20 minutes and was then stirred at room temperature for 24 hours. The mixture was poured into 200 ml of iced water and the mixture was vacuum filtered. The filtrate was extracted with ethyl acetate and the extracts were dried and evaporated to dryness. The residue was crystallized from isopropyl ether to obtain 15.5 g of ethyl (2-cyano-5-methyl-3-thienyl)-oxyacetate melting at 58° C.

STEP B: dimethyl 2-oxo-3-(2-cyano-5-methyl-3-thienyloxy)-propyl phosphonate 50 ml of 1N butyllithium in hexane were added at −60° C. under nitrogen to a mixture of 5.78 g of dimethyl methyl phosphonate in 70 ml of anhydrous tetrahydrofuran and the mixture was stirred for an hour at −60° C. A solution of 10.5 g of the product of Step A in 50 ml of anhydrous tetrahydrofuran was added dropwise at −60° C. to the mixture which was then stirred at −60° C. for 30 minutes. The mixture was evaporated to dryness under reduced pressure at 40° C. and the residue was taken up in 150 ml of water and 150 ml of ethyl acetate. The mixture was acidified to a pH of 4.5 and was decanted. The organic phase was dried and evaporated to dryness to obtain a brown oil. The oil was chromatographed over silica gel and was eluted with a 1-1 acetone-chloroform mixture to obtain 2 g of dimethyl 2-oxo-3-(2-cyano-5-methylthienyloxy)-propyl phosphonate with an Rf = 0.3.

STEP C: ethyl (8RS, 9SR, 12RS)(5Z,13E) 9-acetoxy-15-oxo-16-[3'-(2'-cyano-5'-methyl)-thienyloxy]-17,18,19,20-tetranor-prosta-5,13-dienoate 582 mg of the product of Step B were slowly added under nitrogen to a mixture of 92 mg of sodium hydride in 50% in 7 ml of dimethoxyethane and the mixture was stirred at room temperature for one hour. A mixture of 489 mg of ethyl (1'RS, 2'SR, 5'SR)(5Z) 7-(2'-acetoxy-5'-formyl-1'-cyclopentyl)-5-heptenoate in 5 ml of anhydrous dimethoxyethane was added thereto and the mixture was heated at 50° C. for 4 hours and at 70° C. for 2 hours and was then cooled. The mixture was poured into a saturated monosodium phosphate solution and the mixture was extracted with ethyl acetate. The extracts were dried and evaporated to dryness to obtain 991 mg of raw product which was chromatographed over silica gel. Elution with a 60-40 cyclohexane-ethyl acetate mixture yielded 199 mg of ethyl (8RS, 9SR, 12RS)(5Z,13E) 9-acetoxy-15-oxo-16-[3'-(2'-cyano-5'-methyl)-thienyloxy]-17,18,19,20-tetranor-prosta-5,13-dienoate.

STEP D: ethyl (8RS, 9SR, 12RS, 15RS)(5Z,13E) 9-acetoxy-15-hydroxy-16-[3'-(2'-cyano-5-methyl)-thienyloxy]-17,18,19,20-tetranor-prosta-5,13-dienoate and ethyl (8RS, 9SR, 12RS, 15SR)(5Z,13E) 9-acetoxy-15-hydroxy-16-[3'-(2'-cyano-5'-methyl)-thienyloxy]-17,18,19,20-tetranor-prosta-5,13-dienoate 1.15 ml of 0.22 M of zinc borohydride in dimethoxyethane was added dropwise under nitrogen at 0° C. to a solution of 332 mg of the product of Step C in 16.5 ml of anhydrous dimethoxyethane and the mixture was stirred for 2 hours at 0° C. and was then poured into a saturated monosodium phosphate solution. The mixture was extracted with ethyl acetate and the extracts were dried to obtain 365 mg of raw product. The latter was chromatographed over silica gel and was eluted with an 80-20 benzene-ethyl acetate mixture and then over a plate with a 60-40 benzene-ethyl acetate mixture to obtain 66 mg of ethyl (8RS, 9SR, 12RS, 15RS)(5Z,13E) 9-acetoxy-15-hydroxy-16-[3'-(2'-cyano-5'-methyl)-thienyloxy]-17,18,19,20-tetranor-prosta-5,13-dienoate and 85 mg of ethyl (8RS, 9SR, 12RS, 15SR)(5Z,13E) 9-acetoxy-15-hydroxy-16-[3'-(2'-cyano-5'-methyl)-thienyloxy]-17,18,19,20-tetranor-prosta-5,13-dienoate.

STEP E: (8RS, 9SR, 12RS, 15RS)(5Z,13E) 9,15-dihydroxy-16-[3'-(2'-cyano-5'-methyl)-thienyloxy]-17,18,19,20-tetranor-prosta-5,13-dienoic acid 0.522 ml of N sodium hydroxide was added to a solution of 64 mg of the 15RS isomer of Step D in 2 ml of ethanol and 0.2 ml of water and the mixture was stirred under nitrogen overnight at room temperature and was then evaporated to dryness. The residue was taken up in ethyl acetate and a saturated monosodium phosphate solution was added thereto. The mixture was extracted with ethyl acetate and the extracts were dried and evaporated to dryness to obtain 69 mg of raw product. The product was chromatographed over silica gel and was eluted with ethyl acetate to obtain 40 mg of (8RS, 9SR, 12RS, 15RS)(5Z,13E) 9,15-dihydroxy-16-[3'-(2'-cyano-5'-methyl)-thienyloxy]-17,18,19,20-tetranor-prosta-5,13-dienoic acid with an Rf = 0.15.

EXAMPLE 21 tris(hydroxymethyl)-aminomethane salt of (8RS, 9SR, 12RS, 15RS)(5Z,13E), 9,15-dihydroxy-16-[3'-(5'-chloro)-thienyloxy]-17,18,19,20-tetranor-prosta-5,13-dienoic acid 50 mg of (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid were dissolved in a solution of N/100 tris(hydroxymethyl) methylamine in a 1-1 water-ethanol mixture and after standing for 15 minutes, the mixture was evaporated to dryness to obtain the tris(hydroxymethyl)-aminomethane salt of the said acid. The example was repeated to form the tris(hydroxymethyl)-aminomethane salt of (8RS, 9SR, 12RS, 15SR)(5Z,13E) 9,15-dihydroxy-16-[3'-(5'1 -chloro)-thienyloxy]-17,18,19,20-tetranor-prosta-5,13-dienoic acid, (8RS, 9SR, 12RS, 15RS)(5Z,13E) 9,15-dihydroxy-16-[3'-(2'-chloro)-thienyloxy]-17,18,19,20-tetranor-prosta-5,13-dienoic acid and (8RS, 9SR, 12RS, 15RS)(5Z,13E) 9,15-dihydroxy-16-[3'-(4'-chloro)-thienyloxy]-17,18,19,20-tetranor-prosta-5,13-dienoic acid.

EXAMPLE 22 tris(hydroxymethyl)-aminomethane salt of (8RS, 9SR, 12RS, 15RS)(5Z,13E) 9,15-dihydroxy-16-[3'-(2'-cyano-5'-methyl)-thienyloxy]-17,18,19,20-tetranor-prosta-5,13-dienoic acid 20 mg of (8RS, 9SR, 12RS, 15RS)(5Z,13E) 9,15-dihydroxy-16-[3'-(2'-cyano-5'-methyl)-thienyloxy]-17,18,19,20-tetranor-prosta-5,13-dienoic acid were dissolved in 1 ml of ethanol and a solution of 5.75 g of tris(hydroxymethyl)-aminomethane in 1 ml of water was added thereto. The mixture was stirred for 15 minutes at room temperature and was then evaporated to dryness to obtain 26mg of the tris(hydroxymethyl)aminomethane salt of the said acid.

EXAMPLE 23

22 mg of (8RS, 9SR, 12RS, 15RS)(5Z,13E) 9,15 dihydroxy-16-[3'-(1'-thia-2',5'-diazolyloxy]-17,18,19,20-tetranor-prosta-5,13-dienoic acid were dissolved in a solution of 7 mg of tris(hydroxymethyl)-aminomethane in 1 ml of water and 1 ml of ethanol and the mixture stood for 15 minutes and was evaporated to dryness to obtain the tris(hydroxymethyl)aminomethane salt of the said acid.

EXAMPLE 24

Injectable veterinary compositions were prepared with 2 mg of the tris(hydroxymethyl)-aminomethane salt of either (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid or (8RS, 9SR, 12RS, 15RS)(5Z,13E) 9,15-dihydroxy-16-[3'-thienyloxy]-17,18,19,20-tetranor-prosta-5,13-dienoic acid, 3.2 mg of benzyl alcohol and 1 ml of distilled water.

PHARMACOLOGICAL DATA

The following compounds were tested for their pharmacological activity in the form of their tris(hydroxymethyl)-aminomethane salts: (8RS, 9SR, 12RS, 15RS)(5Z,13E) 9,15-dihydroxy-16-[3'-thienyloxy]-17,18,19,20-tetranor-prosta-5,13-dienoic acid [product A], (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid [product B], (8RS, 9SR, 12RS, 15RS)(5Z,13E) 9,15-dihydroxy-16-[3'-(2'-chlorothienyloxy]-17,18,19,20-tetranor-prosta-5,13-dienoic acid [product C] and (8RS, 9SR, 12RS, 15RS)(5Z,13E) 9,15-dihydroxy-16-[3'-(4'-chloro)-thienyloxy]-17,18,19,20-tetranor-prosta-5,13-dienoic acid [product D].

A. Hypotensive Activity

The products were administered intraveinously as a solution in physiological serum containing 10% of ethanol to rabbits anesthesized with urethane and the carotidine pressure was measured to determine the dose that lowered the pressure 30%. This dose was 2 μg/kg for product A, 10 μg/kg for products B and C and 5 μg/kg for product D.

B. Contracturant Activity

The contracturant activity was determined on the isolated ileon of the guinea pig in a bath containing 10 ml of Tyrode liquid which was constantly oxygenated to determine the dose of the product which would provoke a contraction of the organ comparable to that provoked by 10 ng/ml of acetylcholine. The contracturant dose was 100 ng/ml of product A, 500 ng/ml for product C and 50 ng/ml for product D.

C. Luteolytic Action of Product A

The luteolytic power of these substances was studied with the cycles of cows of French Frisonne Pie Noire race. The plasmatic amount of progesterone was determined every two days except at the moment of presumed luteolysis at which dosages have been practiced every 12 hours. At the beginning of the test properly speaking, the cycles of 15 cows were synchronized with an intramuscular injection of 25 mg of Prostaglandin $F_2\alpha$ and after studying the evolution of the progesterone level, 3 cows out of the 15 were chosen for the test and received 2, 5 or 10 mg of product A by intramuscular injection.

On the day $J_1$, 15 cows received an intramuscular injection of 25 mg of Prostaglandin $F_2\alpha$ and the plasmatic progesterone level was studied at 10 hours. On days $J_2$, $J_3$, $J_4$, the plasmatic progesterone was studied at 10 and 22 hours and on days $J_6$, $J_8$, $J_{12}$, and $J_{13}$, the progesterone was studied at 10 hours. From the said studies, 3 cows were selected which showed an elevated progesterone level from the 15 and on the day $J_{15}$, the 3 cows received an intramuscular injection of 2, 5 or 10 mg product A. The plasmatic progesterone was determined at 10 and 22 hours on days $J_{15}$, $J_{16}$, $J_{17}$ and $J_{18}$ and at 10 hours on days $J_{19}$, $J_{21}$, $J_{23}$ and $J_{25}$. The results from day $J_{13}$ on are reported in the following Table and the plasmatic progesterone was studied by radioimmunology in ng/ml.

| cows Day | | No. 1 Product A 10 mg | No. 2 Product A 5 mg | No. 3 Product A 2 mg |
|---|---|---|---|---|
| $J_{13}$ | 10 h | 6.7 | 4.8 | 3.7 |
| $J_{15}$ | 10 h | 5.8 | 6.0 | 4.7 |
|  | 22 h | 1.5 | 1.2 | 1.5 |
| $J_{16}$ | 10 h | 0.5 | ≦0.7 | 0.7 |
|  | 22 h | ≦0.1 | ≦0.1 | ≦0.1 |
| $J_{17}$ | 10 h | ≦0.1 | ≦0.1 | ≦0.1 |
|  | 22 h | ≦0.1 | ≦0.1 | ≦0.1 |
| $J_{18}$ | 10 h | ≦0.1 | ≦0.1 | ≦0.1 |
|  | 22 h | ≦0.1 | ≦0.1 | ≦0.1 |
| $J_{19}$ | 10 h | ≦0.1 | 0.2 | 0.2 |
| $J_{21}$ | 10 h | 0.4 | ≦0.1 | ≦0.1 |
| $J_{23}$ | 10 h | 0.7 | 0.2 | 0.8 |

-continued

| cows Day | | No. 1 Product A 10 mg | No. 2 Product A 5 mg | No. 3 Product A 2 mg |
|---|---|---|---|---|
| $J_{25}$ | 10 h | 1.7 | 1.3 | 1.4 |

The results of the above Table shown that intramuscular injection of product A provokes at a dose of 2 mg in the animal a luteolysis showed by the rapid drop of the level of progesterone.

D. Luteolytic Activity of Product B

The luteolytic power of these substances was studied on the cycle of cows of the French Frisonne Pie Noire race as for product A with the solution of one cow of out 17 which received an intramuscular dose of 2 mg of product B. The results are reported in the following Table.

| Cow Days | | No. 1 Product B 2 mg |
|---|---|---|
| $J_{13}$ | 10 h | 2.1 |
| $J_{15}$ | 10 h | 3.0 |
|  | 22 h | 1.8 |
| $J_{16}$ | 10 h | 0.7 |
|  | 22 h | 0.3 |
| $J_{17}$ | 10 h | 0.3 |
|  | 22 h | 0.2 |
| $J_{18}$ | 10 h | 0.2 |
|  | 22 h | 0.2 |
| $J_{19}$ | 10 h | 0.4 |
| $J_{21}$ | 10 h | 1.1 |
| $J_{23}$ | 10 h | 3.7 |
| $J_{25}$ | 10 h | 6.0 |

The above Table shows that product B at an intramuscular dose of 2 mg provoked in the cows a luteolysis shown by the sharp drop in the progesterone level.

Various modifications of the products and processes of the invention may be made without departing from the spirit or scope thereof and it is to be understood that the invention is intended to be limited only as defined in the appended claims.

We claim:

1. A compound of the formula

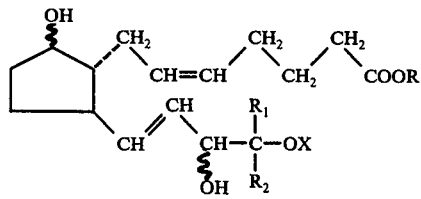

wherein R is selected from the group consisting of hydrogen, alkyl of 1 to 4 carbon atoms, an alkali metal, an equivalent of an alkaline earth metal, magnesium or a pharmaceutically acceptable amine base, $R_1$ and $R_2$ are individually selected from the group consisting of hydrogen and methyl and X is thienyl optionally substituted with at least one member of the group consisting of chlorine, —CN and methyl with the wavy lines indicating that the hydroxy may be in either one of the two possible α and β positions.

2. A compound of claim 1 wherein R is selected from the group consisting of hydrogen and tris(hydroxymethyl)-aminomethane and one of $R_1$ and $R_2$ is hydrogen.

3. A compound of claim 2 wherein X is thienyl.

4. A compound of claim 1 selected from the group consisting of (8RS, 9SR, 12RS, 15RS)(5Z,13E) 9,15-dihydroxy-16-[3'-thienyloxy]-17,18,19,20-tetranor-prosta-5,13-dienoic acid and its tris(hydroxymethyl)-aminomethane salt.

5. A compound of claim 1 selected from the group consisting of (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid and its tris(hydroxymethyl)-aminomethane salt.

6. A compound of claim 1 which is (8RS, 9SR, 12RS, 15RS)(5Z,13E) 9,15-dihydroxy-16-[3'-(4'-chloro)-thienyloxy]-17,18,19,20-tetranor-prosta-5,13-dienoic acid.

7. A compound of claim 1 which is (8RS, 9SR, 12RS, 15RS)(5Z,13E) 9,15-dihydroxy-16-[3'-(2'-chloro)-thienyloxy]-17,18,19,20-tetranor-prosta-5,13-dienoic acid.

8. A compound of claim 1 which is (8RS, 9SR, 12RS, 15RS)(5Z,13E) 9,15-dihydroxy-16-[3'-(2'-cyano-5'-methyl)-thienyloxy]-17,18,19,20-tetranor-5,13-dienoic acid.

9. A compound of claim 1 selected from the group consisting of (8RS, 9SR, 12RS, 15RS)(5Z,13E) 9,15-dihydroxy-16-[3'-thienyloxy]-17,18,19,20-tetranor-prosta-15,13-dienoic acid and its ethyl ester.

10. A compound of claim 1 which is (8RS, 9SR, 12RS, 15SR)(5Z,13E) 9,15-dihydroxy-16-[3'-(5'-chloro)-thienyloxy]-17,18,19,20-tetranor-prosta-5,13-dienoic acid.

11. An hypotensive composition comprising an hypotensively effective amount of at least one compound of claim 1 and an inert pharmaceutical carrier.

12. The composition of claim 11 wherein R is selected from the group consisting of hydrogen and tris(hydroxymethyl) aminomethane and one of $R_1$ and $R_2$ is hydrogen.

13. The composition of claim 12 wherein X is thienyl.

14. A method of relieving hypertension in warm-blooded animals comprising administering to warm-blooded animals an hypotensively effective amount of at least one compound of claim 1.

15. The method of claim 14 wherein R is selected from the group consisting of hydrogen and tris(hydroxymethyl) aminomethane and one of $R_1$ and $R_2$ is hydrogen.

16. The method of claim 15 wherein X is thienyl.

17. The method of claim 14 wherein the compound is selected from the group consisting of (8RS, 9SR, 12RS, 15RS)(5Z,13E) 9,15-dihydroxy-16-[3'-thienyloxy]-17,18,19,20-tetranor-prosta-5,13-dienoic acid and its tris(hydroxymethyl) aminomethane salt.

18. The method of claim 14 wherein the compound is selected from the group consisting of (8RS, 9SR, 12RS, 15RS)(5Z,13E) 9,15-dihydroxy-16-[3'-(5'-chloro)-thienyloxy]-17,18,19,20-tetranor-prosta-5,13-dienoic acid and its tris(hydroxymethyl)-aminomethane salt.

* * * * *